US009463229B2

(12) United States Patent
Lujan

(10) Patent No.: US 9,463,229 B2
(45) Date of Patent: Oct. 11, 2016

(54) MODIFIED PROTOZOAN EXPRESSING AT LEAST TWO VARIABLE SURFACE PROTEINS (VSP), A VACCINE COMPRISING IT AND PROCEDURES, USES, AND METHODS THEREOF

(75) Inventor: Hugo Daniel Lujan, Córdoba (AR)

(73) Assignee: Universidad Catolica de Cordoba, Cordoba (AR)

( * ) Notice: Subject to any disclaimer, the term of this patent is extended or adjusted under 35 U.S.C. 154(b) by 905 days.

(21) Appl. No.: 13/132,468

(22) PCT Filed: Dec. 2, 2009

(86) PCT No.: PCT/IB2009/055470
§ 371 (c)(1),
(2), (4) Date: Aug. 15, 2011

(87) PCT Pub. No.: WO2010/064204
PCT Pub. Date: Jun. 10, 2010

(65) Prior Publication Data
US 2012/0093871 A1    Apr. 19, 2012

(51) Int. Cl.
| | | |
|---|---|---|
| C12N 1/10 | (2006.01) | |
| C12N 1/00 | (2006.01) | |
| A61K 39/00 | (2006.01) | |
| A01N 63/00 | (2006.01) | |
| A61K 48/00 | (2006.01) | |
| A61K 39/002 | (2006.01) | |
| A61K 35/68 | (2006.01) | |
| C07K 14/44 | (2006.01) | |
| C07K 16/20 | (2006.01) | |
| C12N 15/86 | (2006.01) | |
| A61K 38/00 | (2006.01) | |
| C12N 1/20 | (2006.01) | |

(52) U.S. Cl.
CPC ............ *A61K 39/002* (2013.01); *A61K 35/68* (2013.01); *C07K 14/44* (2013.01); *C07K 16/20* (2013.01); *A61K 38/00* (2013.01); *A61K 2039/522* (2013.01); *A61K 2039/542* (2013.01); *A61K 2039/552* (2013.01); *C12N 1/10* (2013.01); *C12N 1/20* (2013.01); *C12N 15/86* (2013.01)

(58) Field of Classification Search
CPC .... A61K 45/06; A61K 39/00; A61K 39/092; A61K 47/4833; A61K 38/00; A61B 5/14532; C12P 19/14; A01N 43/40; A01N 43/78; C07K 14/315; C07K 14/44; C12N 1/10; C12N 1/20; C12N 15/86
See application file for complete search history.

(56) References Cited

PUBLICATIONS

Carranza et al., Infection and Immunity, 2002; 70(9): 5265-5268.*
Sra et al., Dermatologic Therapy, 2004; 17(6): 513-516.*
CDC Leishmaniasis; http://www.cdc.gov/parasites/leishmaniasis/prevent.html; accessed Jan. 9, 2014.*
Yang et al., Molecular and Biochemical Parasitology, 1995; 75: 69-74.*
Burns et al., Vaccine, 2003; 21: 1843-1852.*
Hoppner (Horm Re. 2002, 58 Suppl. 3:7-15).*
Saraiya et al., PLoS Pathog, Nov. 2008; 4(11): 1-10.*
Best, 2005, The Journal of biological chemistry; 280(21): 20573-9.*
Deitsch et al, Microbiol. Mol. Biol. Rev. 61, 281-293 (1997).
Nash et al, Exp. Parasitol. 71, 415-421 (1990).
Macrae et al., Science 311, 195-198 (2006).
Elmendorf et al., Mol. Biochem. Parasitol. 113, 157-169 (2001).
Lujan et al, J. Biol. Chem. 270, 29307-29313 (1995).
Ngo et al, Proc. Natl Acad. Sci. USA 95, 14687-14692 (1998).
Elbashir et al, Genes Dev 15, 188-200 (2001).
Yee et al, Proc. Natl Acad. Sci. USA 92, 5615-5619 (1995).
Aggarwal et al, Cysteinerich; *Mol Biochem Parasitol* 32, 39-47 (1989).
Smith et al,Infect. Immun. May 1982; 36(2): 714-9.
Clark et al, "Methods for cultivation of luminal parasite protists of clinical importance", Clin MicrobiolRev. Jul. 2002; 15(3):329-41.
Baum et al, "A new method for cloning Giardia lamblia, with a discussion of the statistical considerations of limiting dilution", J Parasitol. Apr. 1988; 74(2): 267-9.
Nash, "Surface antigen variability and variation in *Giardia lamblia*", *Parasitol Today* 8, 229-234 (1992).
Touz et al, J Biol Chem. Feb. 21, 2003;278(8):6420-6. Epub Dec. 3, 2002.
Heyworth, "Relative susceptibility of *Giardia muris* trophozoites to killing by mouse antibodies of different isotypes", *J Parasitol* 78, 73-76 (1992).
International Search Report for PCT/IB2009/055470, mailed Sep. 15, 2010.
Written Opinion of the International Searching Authority for PCT/IB2009/055470, mailed Sep. 15, 2010.
Prucca, C.G. et al., "Antigenic variation in Giardia lamblia is regulated by RNA interference", Nature, vol. 456, No. 7223, (Dec. 11, 2008), pp. 750-754.
Carranza, P.G. et al., "Simultaneous expression of different variant-specific surface proteins in single Giardia lamblia trophozoites during encystation", Infection and Immunity, vol. 70, No. 9, (Sep. 2002), pp. 5265-5268.
Nash, T.E. et al., "Variant-specific surface protein switching in Giardia lamblia", Infection and Immunity, vol. 69, No. 3, (Mar. 2001), pp. 1922-1923.
Mowatt, M.R. et al., "Carboxy-terminal sequence conservation among variant-specific surface proteins of Giardia lamblia", Molecular and Biochemical Parasitology, vol. 49, No. 2, (Dec. 1, 1991), pp. 215-227.
Morrison, H.G. et al., "Genomic minimalism in the early diverging intestinal parasite Giardia lamblia", Science, vol. 317, No. 5846, (Sep. 28, 2007), pp. 1921-1926.

(Continued)

*Primary Examiner* — Gary Nickol
*Assistant Examiner* — Lakia Tongue
(74) *Attorney, Agent, or Firm* — RatnerPrestia

(57) ABSTRACT

Modified protozoa parasites comprising simultaneous expression on its surface of at least two variable surface proteins (VSP). The modified protozoa may also simultaneously express the complete repertoire of variable surface proteins. Protozoa show reduced expression of Dicer, RNA-dependant RNA-polymerase (RdRP) enzymes or both, wherein the RdRP gene and/or the Dicer gene has been silenced. The protozoan may be any protozoan showing an antigenic variation mechanism.

8 Claims, 16 Drawing Sheets

(56) References Cited

PUBLICATIONS

Adam, R.D. et al., "Biology of Giardia lamblia", Clinical Microbiology, vol. 14, No. 3, (Jul. 2001), pp. 447-475.

Rivero, F.D. et al., "Disruption of antigenic variation is crucial for effective parasite vaccine", Nature Medicine, vol. 16, No. 5, (May 2010), p. 551.

Jambhekar et al, "Cis-acting determinants of asymmetric, cytoplasmic RNA transport", RNA13, pp. 625-642 (2007).

Gottstein et al, "In vitro synthesized immunoglobulin A from nu/ + and reconstituted nu/nu mice against a dominant surface antigen of Giardia lamblia", Parasitol Res 79:644-648 (1993).

Lujan et al, "Increased expression of the molecular chaperone BiP/GRP78 during the differentiation of a primitive eukaryote", Biol Cell (1996) 86, 11-18.

Touz et al, "Identification and Characterization of a Novel Secretory Granule Calcium-binding Protein from the Early Branching Eukaryote *Giardia lamblia*", The Journal of Biological Chemistry, vol. 277, No. 52, pp. 50557-50563 (2002).

Nash, "Antigenic variation in *Giardia lamblia* and the host's immune response", Phil. Trans. R. Soc. Lond. B (1997), 352, 1369-1375.

Hutvagner et al, "Detailed characterization of the post-transcriptional gene-silencing-related small RNA and a GUS gene-silenced tobacco", RNA (2000), 6:1445-1454.

Mowatt et al, "Developmentally regulated expression of a Giardia lamblia cyst wall protein gene", Molecular Microbiology (1995) 15(5), 955-963.

Elbashir et al, "Duplexes of 21—nucleotide RNAs mediate RNA interference in cultured mammalian cells", Nature, vol. 411, May 24, 2001, pp. 494-498.

Lujan et al, "Purification of a Variant-specific Surface Protein of *Giardia lamblia* and Characterization of its Metal-binding Properties", The Journal of Biological Chemistry, vol. 270, No. 23, pp. 13807-13813, 1995.

\* cited by examiner

Percentage of positive troophozoites for each VSP

Figure 13

```
                       SEQUENCE LISTING

<160> NUMBER OF SEQ ID NOS: 146

<210> SEQ ID NO 1
<211> LENGTH: 25
<212> TYPE: DNA
<213> ORGANISM: Giardia intestinalis

<400> SEQUENCE: 1
gttttgttct cgcggggta ctcgt                                           25

<210> SEQ ID NO 2
<211> LENGTH: 23
<212> TYPE: DNA
<213> ORGANISM: Giardia intestinalis

<400> SEQUENCE: 2
agagcgcgcg gctcaatgcg cag                                            23

<210> SEQ ID NO 3
<211> LENGTH: 23
<212> TYPE: DNA
<213> ORGANISM: Giardia intestinalis

<400> SEQUENCE: 3
gattgcatgg gcaggaaaag caa                                            23

<210> SEQ ID NO 4
<211> LENGTH: 23
<212> TYPE: DNA
<213> ORGANISM: Giardia intestinalis

<400> SEQUENCE: 4
tctcgatgta acacaggatt tgt                                            23

<210> SEQ ID NO 5
<211> LENGTH: 23
<212> TYPE: DNA
<213> ORGANISM: Giardia intestinalis
<220> FEATURE:
<221> NAME/KEY: misc_feature
<222> LOCATION: (16)..(17)
<223> OTHER INFORMATION: n is a, c, g, or t

<400> SEQUENCE: 5
ggacaatgtg cagacnnaga agg                                            23

<210> SEQ ID NO 6
<211> LENGTH: 24
<212> TYPE: DNA
<213> ORGANISM: Giardia intestinalis

<400> SEQUENCE: 6
aaagatggct ccggaggcga taca                                           24

<210> SEQ ID NO 7
```

<211> LENGTH: 24
<212> TYPE: DNA
<213> ORGANISM: Giardia intestinalis

<400> SEQUENCE: 7
cagacctgtg gacagtgcgc cgag                                          24

<210> SEQ ID NO 8
<211> LENGTH: 23
<212> TYPE: DNA
<213> ORGANISM: Giardia intestinalis

<400> SEQUENCE: 8
ctttcatgta caagggcggc tgt                                           23

<210> SEQ ID NO 9
<211> LENGTH: 25
<212> TYPE: DNA
<213> ORGANISM: Giardia intestinalis
<220> FEATURE:
<221> NAME/KEY: misc_feature
<222> LOCATION: (8)..(8)
<223> OTHER INFORMATION: n is a, c, g, or t

<400> SEQUENCE: 9
cgaagcancc cagcagcccg gacag                                         25

<210> SEQ ID NO 10
<211> LENGTH: 23
<212> TYPE: DNA
<213> ORGANISM: Giardia intestinalis

<400> SEQUENCE: 10
gcaaggatac ttcgtgccgc cgg                                           23

<210> SEQ ID NO 11
<211> LENGTH: 24
<212> TYPE: DNA
<213> ORGANISM: Giardia intestinalis

<400> SEQUENCE: 11
accaatcggt cataccatgc ggag                                          24

<210> SEQ ID NO 12
<211> LENGTH: 25
<212> TYPE: DNA
<213> ORGANISM: Giardia intestinalis

<400> SEQUENCE: 12
acgataaaaa gtacaagggc gtgct                                         25

<210> SEQ ID NO 13
<211> LENGTH: 23
<212> TYPE: DNA
<213> ORGANISM: Giardia intestinalis

<400> SEQUENCE: 13
accggcacca agacgtgcaa gac                                           23

<210> SEQ ID NO 14
<211> LENGTH: 24
<212> TYPE: DNA
<213> ORGANISM: Giardia intestinalis

<400> SEQUENCE: 14

```
tgcgacgtgc gagaagggcg ccga                                              24

<210> SEQ ID NO 15
<211> LENGTH: 25
<212> TYPE: DNA
<213> ORGANISM: Giardia intestinalis
<220> FEATURE:
<221> NAME/KEY: misc_feature
<222> LOCATION: (10)..(11)
<223> OTHER INFORMATION: n is a, c, g, or t

<400> SEQUENCE: 15
gcccgacccn nagtgcaaca ccccc                                             25

<210> SEQ ID NO 16
<211> LENGTH: 24
<212> TYPE: DNA
<213> ORGANISM: Giardia intestinalis

<400> SEQUENCE: 16
gctgcaagac gtgcagtgag ccga                                              24

<210> SEQ ID NO 17
<211> LENGTH: 23
<212> TYPE: DNA
<213> ORGANISM: Giardia intestinalis
<220> FEATURE:
<221> NAME/KEY: misc_feature
<222> LOCATION: (21)..(21)
<223> OTHER INFORMATION: n is a, c, g, or t

<400> SEQUENCE: 17
agacaagcaa ggaggtgtgc nca                                               23

<210> SEQ ID NO 18
<211> LENGTH: 23
<212> TYPE: DNA
<213> ORGANISM: Giardia intestinalis

<400> SEQUENCE: 18
acggttgtga gcacctggaa ggc                                               23

<210> SEQ ID NO 19
<211> LENGTH: 23
<212> TYPE: DNA
<213> ORGANISM: Giardia intestinalis

<400> SEQUENCE: 19
cctgtgccaa gtgcaatacc tcg                                               23

<210> SEQ ID NO 20
<211> LENGTH: 24
<212> TYPE: DNA
<213> ORGANISM: Giardia intestinalis

<400> SEQUENCE: 20
agctacgaag gagagggcac gggg                                              24

<210> SEQ ID NO 21
<211> LENGTH: 24
<212> TYPE: DNA
<213> ORGANISM: Giardia intestinalis

<400> SEQUENCE: 21
```

```
tcggcccgca cagcctcctg ccag                                          24

<210> SEQ ID NO 22
<211> LENGTH: 24
<212> TYPE: DNA
<213> ORGANISM: Giardia intestinalis
<220> FEATURE:
<221> NAME/KEY: misc_feature
<222> LOCATION: (14)..(14)
<223> OTHER INFORMATION: n is a, c, g, or t

<400> SEQUENCE: 22
acgaaacgac caanctccct ggaa                                          24

<210> SEQ ID NO 23
<211> LENGTH: 25
<212> TYPE: DNA
<213> ORGANISM: Giardia intestinalis

<400> SEQUENCE: 23
tgaataatgg cgcgctcatc acttg                                         25

<210> SEQ ID NO 24
<211> LENGTH: 23
<212> TYPE: DNA
<213> ORGANISM: Giardia intestinalis

<400> SEQUENCE: 24
gatgtaagac gtgcaccagc cag                                           23

<210> SEQ ID NO 25
<211> LENGTH: 23
<212> TYPE: DNA
<213> ORGANISM: Giardia intestinalis

<400> SEQUENCE: 25
tactacctgt ccaagaaaa gtg                                            23

<210> SEQ ID NO 26
<211> LENGTH: 23
<212> TYPE: DNA
<213> ORGANISM: Giardia intestinalis

<400> SEQUENCE: 26
cccccaacca acaataaagg gcc                                           23

<210> SEQ ID NO 27
<211> LENGTH: 23
<212> TYPE: DNA
<213> ORGANISM: Giardia intestinalis
<220> FEATURE:
<221> NAME/KEY: misc_feature
<222> LOCATION: (16)..(17)
<223> OTHER INFORMATION: n is a, c, g, or t

<400> SEQUENCE: 27
acctcataca gaacannaac agg                                           23

<210> SEQ ID NO 28
<211> LENGTH: 23
<212> TYPE: DNA
<213> ORGANISM: Giardia intestinalis

<400> SEQUENCE: 28
gggatctccg tcgctgtcat cgc                                           23
```

```
<210> SEQ ID NO 29
<211> LENGTH: 23
<212> TYPE: DNA
<213> ORGANISM: Giardia intestinalis
<220> FEATURE:
<221> NAME/KEY: misc_feature
<222> LOCATION: (21)..(21)
<223> OTHER INFORMATION: n is a, c, g, or t

<400> SEQUENCE: 29
tgctggtggt tcatatgtag ngg                                      23

<210> SEQ ID NO 30
<211> LENGTH: 22
<212> TYPE: DNA
<213> ORGANISM: Giardia intestinalis

<400> SEQUENCE: 30
gcaagcactc ttgcaggagc tt                                       22

<210> SEQ ID NO 31
<211> LENGTH: 23
<212> TYPE: DNA
<213> ORGANISM: Giardia intestinalis

<400> SEQUENCE: 31
gctctacgac tcaggctaat tgt                                      23

<210> SEQ ID NO 32
<211> LENGTH: 24
<212> TYPE: DNA
<213> ORGANISM: Giardia intestinalis

<400> SEQUENCE: 32
caacggggtg tgtgaagcag ccgc                                     24

<210> SEQ ID NO 33
<211> LENGTH: 23
<212> TYPE: DNA
<213> ORGANISM: Giardia intestinalis

<400> SEQUENCE: 33
gtaagaagtg ccttctgcaa acc                                      23

<210> SEQ ID NO 34
<211> LENGTH: 23
<212> TYPE: DNA
<213> ORGANISM: Giardia intestinalis

<400> SEQUENCE: 34
caaaccttca tgttcaaggg cgg                                      23

<210> SEQ ID NO 35
<211> LENGTH: 24
<212> TYPE: DNA
<213> ORGANISM: Giardia intestinalis

<400> SEQUENCE: 35
tgatgctgcc tctggtacta ctgg                                     24

<210> SEQ ID NO 36
<211> LENGTH: 24
<212> TYPE: DNA
```

<213> ORGANISM: Giardia intestinalis

<400> SEQUENCE: 36
gcggctgata ccacggattc ctgt                                         24

<210> SEQ ID NO 37
<211> LENGTH: 23
<212> TYPE: DNA
<213> ORGANISM: Giardia intestinalis

<400> SEQUENCE: 37
caactggggt cacgattggt gag                                          23

<210> SEQ ID NO 38
<211> LENGTH: 24
<212> TYPE: DNA
<213> ORGANISM: Giardia intestinalis
<220> FEATURE:
<221> NAME/KEY: misc_feature
<222> LOCATION: (13)..(14)
<223> OTHER INFORMATION: n is a, c, g, or t

<400> SEQUENCE: 38
actaattgcg ttnngtgtac caaa                                         24

<210> SEQ ID NO 39
<211> LENGTH: 24
<212> TYPE: DNA
<213> ORGANISM: Giardia intestinalis

<400> SEQUENCE: 39
gagtgtgctt ccaatctgta tctg                                         24

<210> SEQ ID NO 40
<211> LENGTH: 25
<212> TYPE: DNA
<213> ORGANISM: Giardia intestinalis

<400> SEQUENCE: 40
gaaacttgca agacaggata tttcc                                        25

<210> SEQ ID NO 41
<211> LENGTH: 23
<212> TYPE: DNA
<213> ORGANISM: Giardia intestinalis
<220> FEATURE:
<221> NAME/KEY: misc_feature
<222> LOCATION: (6)..(6)
<223> OTHER INFORMATION: n is a, c, g, or t

<400> SEQUENCE: 41
tttccntaat gataacgctg ata                                          23

<210> SEQ ID NO 42
<211> LENGTH: 24
<212> TYPE: DNA
<213> ORGANISM: Giardia intestinalis

<400> SEQUENCE: 42
ccggtgctat tcttatcacc tgca                                         24

<210> SEQ ID NO 43
<211> LENGTH: 23
<212> TYPE: DNA
<213> ORGANISM: Giardia intestinalis

```
<400> SEQUENCE: 43
gcaaggacga caacactgcg gcc                                        23

<210> SEQ ID NO 44
<211> LENGTH: 23
<212> TYPE: DNA
<213> ORGANISM: Giardia intestinalis
<220> FEATURE:
<221> NAME/KEY: misc_feature
<222> LOCATION: (22)..(22)
<223> OTHER INFORMATION: n is a, c, g, or t

<400> SEQUENCE: 44
gtatcgcaga gtgcacggga ang                                        23

<210> SEQ ID NO 45
<211> LENGTH: 24
<212> TYPE: DNA
<213> ORGANISM: Giardia intestinalis

<400> SEQUENCE: 45
ggcagtgcac agctagcata gcag                                       24

<210> SEQ ID NO 46
<211> LENGTH: 23
<212> TYPE: DNA
<213> ORGANISM: Giardia intestinalis

<400> SEQUENCE: 46
cctttgcgtg tcggccgaaa cag                                        23

<210> SEQ ID NO 47
<211> LENGTH: 25
<212> TYPE: DNA
<213> ORGANISM: Giardia intestinalis

<400> SEQUENCE: 47
taaaaccaac ggagtttgca ctgcc                                      25

<210> SEQ ID NO 48
<211> LENGTH: 23
<212> TYPE: DNA
<213> ORGANISM: Giardia intestinalis

<400> SEQUENCE: 48
ctatcaggct gagaagtttc ctg                                        23

<210> SEQ ID NO 49
<211> LENGTH: 24
<212> TYPE: DNA
<213> ORGANISM: Giardia intestinalis

<400> SEQUENCE: 49
gcaggaaagt gcacgacctg tgcg                                       24

<210> SEQ ID NO 50
<211> LENGTH: 24
<212> TYPE: DNA
<213> ORGANISM: Giardia intestinalis

<400> SEQUENCE: 50
ggaaaccttg gtaggattat ttgc                                       24
```

```
<210> SEQ ID NO 51
<211> LENGTH: 24
<212> TYPE: DNA
<213> ORGANISM: Giardia intestinalis

<400> SEQUENCE: 51
aatgctaatc tgtacctgaa ggct                                          24

<210> SEQ ID NO 52
<211> LENGTH: 23
<212> TYPE: DNA
<213> ORGANISM: Giardia intestinalis

<400> SEQUENCE: 52
ggcatagatg ggtgctctgc atg                                           23

<210> SEQ ID NO 53
<211> LENGTH: 23
<212> TYPE: DNA
<213> ORGANISM: Giardia intestinalis

<400> SEQUENCE: 53
acaaagggaa catgcattgc aga                                           23

<210> SEQ ID NO 54
<211> LENGTH: 24
<212> TYPE: DNA
<213> ORGANISM: Giardia intestinalis
<220> FEATURE:
<221> NAME/KEY: misc_feature
<222> LOCATION: (12)..(12)
<223> OTHER INFORMATION: n is a, c, g, or t

<400> SEQUENCE: 54
acgccggata anaccaacgg agtt                                          24

<210> SEQ ID NO 55
<211> LENGTH: 22
<212> TYPE: DNA
<213> ORGANISM: Giardia intestinalis
<220> FEATURE:
<221> NAME/KEY: misc_feature
<222> LOCATION: (8)..(9)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 55
tgtgcaanng ataacactaa na                                            22

<210> SEQ ID NO 56
<211> LENGTH: 23
<212> TYPE: DNA
<213> ORGANISM: Giardia intestinalis

<400> SEQUENCE: 56
ctcgtcggct tcctctgctg gtg                                           23

<210> SEQ ID NO 57
<211> LENGTH: 23
<212> TYPE: DNA
<213> ORGANISM: Giardia intestinalis

<400> SEQUENCE: 57
``` accccccgcga gaacaaaact gcc                                          23

<210> SEQ ID NO 58
<211> LENGTH: 23
<212> TYPE: DNA
<213> ORGANISM: Giardia intestinalis

<400> SEQUENCE: 58
tcctgcccat gcaatctgga cga                                           23

<210> SEQ ID NO 59
<211> LENGTH: 25
<212> TYPE: DNA
<213> ORGANISM: Giardia intestinalis

<400> SEQUENCE: 59
attgagccgc gcgctctgtt gcttt                                         25

<210> SEQ ID NO 60
<211> LENGTH: 24
<212> TYPE: DNA
<213> ORGANISM: Giardia intestinalis

<400> SEQUENCE: 60
atgcttcctc tgcgcaatta gtgt                                          24

<210> SEQ ID NO 61
<211> LENGTH: 23
<212> TYPE: DNA
<213> ORGANISM: Giardia intestinalis

<400> SEQUENCE: 61
caatacaatt taccaccgat cag                                           23

<210> SEQ ID NO 62
<211> LENGTH: 23
<212> TYPE: DNA
<213> ORGANISM: Giardia intestinalis

<400> SEQUENCE: 62
tgcacattgt ccattgatag gaa                                           23

<210> SEQ ID NO 63
<211> LENGTH: 23
<212> TYPE: DNA
<213> ORGANISM: Giardia intestinalis

<400> SEQUENCE: 63
ctgatcagct gtatcgcctc cgg                                           23

<210> SEQ ID NO 64
<211> LENGTH: 23
<212> TYPE: DNA
<213> ORGANISM: Giardia intestinalis

<400> SEQUENCE: 64
gtaacagccg cccttgtaca tga                                           23

<210> SEQ ID NO 65
<211> LENGTH: 23
<212> TYPE: DNA
<213> ORGANISM: Giardia intestinalis
<220> FEATURE:

```
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (17)..(18)
<223> OTHER INFORMATION: n is a, c, g, or t

<400> SEQUENCE: 65
catctgccgc cngacanntg gtc                                             23

<210> SEQ ID NO 66
<211> LENGTH: 23
<212> TYPE: DNA
<213> ORGANISM: Giardia intestinalis

<400> SEQUENCE: 66
cccggcggca cgaagtatcc ttg                                             23

<210> SEQ ID NO 67
<211> LENGTH: 23
<212> TYPE: DNA
<213> ORGANISM: Giardia intestinalis

<400> SEQUENCE: 67
accgattggt gagaggcgtc tgc                                             23

<210> SEQ ID NO 68
<211> LENGTH: 24
<212> TYPE: DNA
<213> ORGANISM: Giardia intestinalis

<400> SEQUENCE: 68 acttttatc gttcttaact gtta                                             24

<210> SEQ ID NO 69
<211> LENGTH: 23
<212> TYPE: DNA
<213> ORGANISM: Giardia intestinalis

<400> SEQUENCE: 69
tgtgggagcg taacaccgag tgc                                             23

<210> SEQ ID NO 70
<211> LENGTH: 23
<212> TYPE: DNA
<213> ORGANISM: Giardia intestinalis

<400> SEQUENCE: 70
cacgcagtac acgtggcggc ctt                                             23

<210> SEQ ID NO 71
<211> LENGTH: 23
<212> TYPE: DNA
<213> ORGANISM: Giardia intestinalis

<400> SEQUENCE: 71
cacgcaggag gtggctgagt cct                                             23

<210> SEQ ID NO 72
<211> LENGTH: 23
<212> TYPE: DNA
<213> ORGANISM: Giardia intestinalis

<400> SEQUENCE: 72
```
gtgccggtgc actcttcttc tgt                                          23

<210> SEQ ID NO 73
<211> LENGTH: 23
<212> TYPE: DNA
<213> ORGANISM: Giardia intestinalis

<400> SEQUENCE: 73
ttgtttggct ggaccttctt att                                          23

<210> SEQ ID NO 74
<211> LENGTH: 24
<212> TYPE: DNA
<213> ORGANISM: Giardia intestinalis

<400> SEQUENCE: 74
gcactcaccg tctccgggca cttt                                         24

<210> SEQ ID NO 75
<211> LENGTH: 23
<212> TYPE: DNA
<213> ORGANISM: Giardia intestinalis

<400> SEQUENCE: 75
gcttcttcgt gcaccggtg ccc                                           23

<210> SEQ ID NO 76
<211> LENGTH: 24
<212> TYPE: DNA
<213> ORGANISM: Giardia intestinalis
<220> FEATURE:
<221> NAME/KEY: misc_feature
<222> LOCATION: (17)..(18)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 76
ctggtgccct cgtagtnncc tncc                                         24

<210> SEQ ID NO 77
<211> LENGTH: 23
<212> TYPE: DNA
<213> ORGANISM: Giardia intestinalis

<400> SEQUENCE: 77
tgaggacctg cttaggctcg cag                                          23

<210> SEQ ID NO 78
<211> LENGTH: 24
<212> TYPE: DNA
<213> ORGANISM: Giardia intestinalis
<220> FEATURE:
<221> NAME/KEY: misc_feature
<222> LOCATION: (10)..(10)
<223> OTHER INFORMATION: n is a, c, g, or t

<400> SEQUENCE: 78
cttcttgacn cacacgccgt tctc                                         24

<210> SEQ ID NO 79
<211> LENGTH: 23
<212> TYPE: DNA

<213> ORGANISM: Giardia intestinalis

<400> SEQUENCE: 79
tagcagcccc cgttcatgcg gaa                                          23

<210> SEQ ID NO 80
<211> LENGTH: 24
<212> TYPE: DNA
<213> ORGANISM: Giardia intestinalis

<400> SEQUENCE: 80
acctcctcac agacgctctt tcca                                         24

<210> SEQ ID NO 81
<211> LENGTH: 23
<212> TYPE: DNA
<213> ORGANISM: Giardia intestinalis

<400> SEQUENCE: 81
gcttgtatcc gtcggccgga gtc                                          23

<210> SEQ ID NO 82
<211> LENGTH: 23
<212> TYPE: DNA
<213> ORGANISM: Giardia intestinalis

<400> SEQUENCE: 82
cactcggagc acccagtggc gca                                          23

<210> SEQ ID NO 83
<211> LENGTH: 24
<212> TYPE: DNA
<213> ORGANISM: Giardia intestinalis

<400> SEQUENCE: 83
cacttggtgg cgtcgtccgc attg                                         24

<210> SEQ ID NO 84
<211> LENGTH: 25
<212> TYPE: DNA
<213> ORGANISM: Giardia intestinalis
<220> FEATURE:
<221> NAME/KEY: misc_feature
<222> LOCATION: (7)..(7)
<223> OTHER INFORMATION: n is a, c, g, or t

<400> SEQUENCE: 84
acagcgncgg agatccccgc tatgg                                        25

<210> SEQ ID NO 85
<211> LENGTH: 22
<212> TYPE: DNA
<213> ORGANISM: Giardia intestinalis

<400> SEQUENCE: 85
agaggaagcc cacgaggccc cc                                           22

<210> SEQ ID NO 86
<211> LENGTH: 22
<212> TYPE: DNA
<213> ORGANISM: Giardia intestinalis

<400> SEQUENCE: 86
ggcaattaat taatagaaac at                                           22

<210> SEQ ID NO 87
<211> LENGTH: 23
<212> TYPE: DNA
<213> ORGANISM: Giardia intestinalis

<400> SEQUENCE: 87
gctattaggc aattaattaa tag                                          23

<210> SEQ ID NO 88
<211> LENGTH: 23
<212> TYPE: DNA
<213> ORGANISM: Giardia intestinalis

<400> SEQUENCE: 88
ttccgcaaca caattagcct gag                                          23

<210> SEQ ID NO 89
<211> LENGTH: 23
<212> TYPE: DNA
<213> ORGANISM: Giardia intestinalis

<400> SEQUENCE: 89
tgcactttgt attactactg gcg                                          23

<210> SEQ ID NO 90
<211> LENGTH: 23
<212> TYPE: DNA
<213> ORGANISM: Giardia intestinalis

<400> SEQUENCE: 90
gcacttctta caagtctgat cag                                          23

<210> SEQ ID NO 91
<211> LENGTH: 23
<212> TYPE: DNA
<213> ORGANISM: Giardia intestinalis
<220> FEATURE:
<221> NAME/KEY: misc_feature
<222> LOCATION: (14)..(15)
<223> OTHER INFORMATION: n is a, c, g, or t

<400> SEQUENCE: 91
ttaaattacc agtnnctccc gct                                          23

<210> SEQ ID NO 92
<211> LENGTH: 24
<212> TYPE: DNA
<213> ORGANISM: Giardia intestinalis

<400> SEQUENCE: 92
attactctca ccaatcgtga cccc                                         24

<210> SEQ ID NO 93
<211> LENGTH: 23
<212> TYPE: DNA
<213> ORGANISM: Giardia intestinalis
<220> FEATURE:
<221> NAME/KEY: misc_feature
<222> LOCATION: (5)..(5)
<223> OTHER INFORMATION: n is a, c, g, or t

<400> SEQUENCE: 93
gcgtnatcat tagggaaata tcc                                          23

```
<210> SEQ ID NO 94
<211> LENGTH: 24
<212> TYPE: DNA
<213> ORGANISM: Giardia intestinalis
<220> FEATURE:
<221> NAME/KEY: misc_feature
<222> LOCATION: (8)..(9)
<223> OTHER INFORMATION: n is a, c, g, or t

<400> SEQUENCE: 94
ttaagggnnc tcaggctatt cgtg                                              24

<210> SEQ ID NO 95
<211> LENGTH: 23
<212> TYPE: DNA
<213> ORGANISM: Giardia intestinalis
<220> FEATURE:
<221> NAME/KEY: misc_feature
<222> LOCATION: (14)..(14)
<223> OTHER INFORMATION: n is a, c, g, or t

<400> SEQUENCE: 95
tcaggacaga cccnggtag cag                                                23

<210> SEQ ID NO 96
<211> LENGTH: 23
<212> TYPE: DNA
<213> ORGANISM: Giardia intestinalis

<400> SEQUENCE: 96
cgtcggcgca gttttccaaa tac                                               23

<210> SEQ ID NO 97
<211> LENGTH: 25
<212> TYPE: DNA
<213> ORGANISM: Giardia intestinalis

<400> SEQUENCE: 97
agtgcaaact ccgttggttt tatcc                                             25

<210> SEQ ID NO 98
<211> LENGTH: 23
<212> TYPE: DNA
<213> ORGANISM: Giardia intestinalis

<400> SEQUENCE: 98
gcatcggctg tcgtgcacaa cgt                                               23

<210> SEQ ID NO 99
<211> LENGTH: 23
<212> TYPE: DNA
<213> ORGANISM: Giardia intestinalis
<220> FEATURE:
<221> NAME/KEY: misc_feature
<222> LOCATION: (12)..(12)
<223> OTHER INFORMATION: n is a, c, g, or t

<400> SEQUENCE: 99
gccgctggtc tngacgtagc agg                                               23

<210> SEQ ID NO 100
<211> LENGTH: 24
<212> TYPE: DNA
<213> ORGANISM: Giardia intestinalis

<400> SEQUENCE: 100
```

```
agtcgtagag caagctcctg caag                                              24

<210> SEQ ID NO 101
<211> LENGTH: 24
<212> TYPE: DNA
<213> ORGANISM: Giardia intestinalis

<400> SEQUENCE: 101
accccgttga tgggcacata gttt                                              24

<210> SEQ ID NO 102
<211> LENGTH: 25
<212> TYPE: DNA
<213> ORGANISM: Giardia intestinalis
<220> FEATURE:
<221> NAME/KEY: misc_feature
<222> LOCATION: (11)..(12)
<223> OTHER INFORMATION: n is a, c, g, or t

<400> SEQUENCE: 102
cttccgtctt nnaaataatc ctacc                                             25

<210> SEQ ID NO 103
<211> LENGTH: 23
<212> TYPE: DNA
<213> ORGANISM: Giardia intestinalis

<400> SEQUENCE: 103
gaatcgtaac cccggttgcg tcg                                               23

<210> SEQ ID NO 104
<211> LENGTH: 23
<212> TYPE: DNA
<213> ORGANISM: Giardia intestinalis

<400> SEQUENCE: 104
acttagcaca accggccaca ccc                                               23

<210> SEQ ID NO 105
<211> LENGTH: 24
<212> TYPE: DNA
<213> ORGANISM: Giardia intestinalis

<400> SEQUENCE: 105
cttatcagcc gtactacagg taag                                              24

<210> SEQ ID NO 106
<211> LENGTH: 23
<212> TYPE: DNA
<213> ORGANISM: Giardia intestinalis

<400> SEQUENCE: 106
acggtgctag ccctagttgt aga                                               23

<210> SEQ ID NO 107
<211> LENGTH: 25
<212> TYPE: DNA
<213> ORGANISM: Giardia intestinalis
<220> FEATURE:
<221> NAME/KEY: misc_feature
<222> LOCATION: (13)..(14)
<223> OTHER INFORMATION: n is a, c, g, or t

<400> SEQUENCE: 107
```

```
cgttcttcaa ggnnctcaga ttgtt                                              25
```

<210> SEQ ID NO 108
<211> LENGTH: 22
<212> TYPE: DNA
<213> ORGANISM: Giardia intestinalis

<400> SEQUENCE: 108

```
ctctgcaatg catgttccct tt                                                 22
```

<210> SEQ ID NO 109
<211> LENGTH: 24
<212> TYPE: DNA
<213> ORGANISM: Giardia intestinalis

<400> SEQUENCE: 109

```
cgacccgggt ggtgccgctc ttgc                                               24
```

<210> SEQ ID NO 110
<211> LENGTH: 23
<212> TYPE: DNA
<213> ORGANISM: Giardia intestinalis
<220> FEATURE:
<221> NAME/KEY: misc_feature
<222> LOCATION: (13)..(13)
<223> OTHER INFORMATION: n is a, c, g, or t

<400> SEQUENCE: 110

```
ccattgctgt ctntatcttg ccc                                                23
```

<210> SEQ ID NO 111
<211> LENGTH: 22
<212> TYPE: DNA
<213> ORGANISM: Giardia intestinalis
<220> FEATURE:
<221> NAME/KEY: misc_feature
<222> LOCATION: (11)..(11)
<223> OTHER INFORMATION: n is a, c, g, or t

<400> SEQUENCE: 111

```
gtgttatctt ngcacacgat gc                                                 22
```

<210> SEQ ID NO 112
<211> LENGTH: 24
<212> TYPE: DNA
<213> ORGANISM: Giardia intestinalis

<400> SEQUENCE: 112

```
gacgggagta gaactctgag gaga                                               24
```

<210> SEQ ID NO 113
<211> LENGTH: 16
<212> TYPE: DNA
<213> ORGANISM: Artificial Sequence
<220> FEATURE:
<223> OTHER INFORMATION: primer sense S1

<400> SEQUENCE: 113

```
cvtgtgchrr stgcaa                                                        16
```

<210> SEQ ID NO 114
<211> LENGTH: 17
<212> TYPE: DNA
<213> ORGANISM: Artificial Sequence
<220> FEATURE:
<223> OTHER INFORMATION: primer sense S2

```
<400> SEQUENCE: 114
tgcacsrsct gcyabcc                                                    17

<210> SEQ ID NO 115
<211> LENGTH: 17
<212> TYPE: DNA
<213> ORGANISM: Artificial Sequence
<220> FEATURE:
<223> OTHER INFORMATION: primer sense S3

<400> SEQUENCE: 115
tagtgydsyv mvtgyaa                                                    17

<210> SEQ ID NO 116
<211> LENGTH: 18
<212> TYPE: DNA
<213> ORGANISM: Artificial Sequence
<220> FEATURE:
<223> OTHER INFORMATION: primer sense S4

<400> SEQUENCE: 116
cgatcatgac gggcttct                                                   18

<210> SEQ ID NO 117
<211> LENGTH: 20
<212> TYPE: DNA
<213> ORGANISM: Artificial Sequence
<220> FEATURE:
<223> OTHER INFORMATION: primer antisense R1

<400> SEQUENCE: 117
ccbacgaggc cyccsacgac                                                 20

<210> SEQ ID NO 118
<211> LENGTH: 20
<212> TYPE: DNA
<213> ORGANISM: Artificial Sequence
<220> FEATURE:
<223> OTHER INFORMATION: primer antisense R2

<400> SEQUENCE: 118
cgccttccck ckrcakayga                                                 20

<210> SEQ ID NO 119
<211> LENGTH: 22
<212> TYPE: DNA
<213> ORGANISM: Artificial Sequence
<220> FEATURE:
<223> OTHER INFORMATION: primer sense vsp1267

<400> SEQUENCE: 119
atgttgttga tagccttcta tc                                              22

<210> SEQ ID NO 120
<211> LENGTH: 22
<212> TYPE: DNA
<213> ORGANISM: Artificial Sequence
<220> FEATURE:
<223> OTHER INFORMATION: primer antisense vsp1267

<400> SEQUENCE: 120
ctacgccttc cccctgcata tg                                              22

<210> SEQ ID NO 121
```

```
<211> LENGTH: 21
<212> TYPE: DNA
<213> ORGANISM: Artificial Sequence
<220> FEATURE:
<223> OTHER INFORMATION: primer sense vsp9B10

<400> SEQUENCE: 121
atgtttggca gttttgttct c                                              21

<210> SEQ ID NO 122
<211> LENGTH: 22
<212> TYPE: DNA
<213> ORGANISM: Artificial Sequence
<220> FEATURE:
<223> OTHER INFORMATION: primer antisense vsp9B10

<400> SEQUENCE: 122
tcacgccttc cctctacata tg                                             22

<210> SEQ ID NO 123
<211> LENGTH: 21
<212> TYPE: DNA
<213> ORGANISM: Artificial Sequence
<220> FEATURE:
<223> OTHER INFORMATION: primer HL60 gDicer

<400> SEQUENCE: 123
tggcggcgtc gtatcagtta t                                              21

<210> SEQ ID NO 124
<211> LENGTH: 19
<212> TYPE: DNA
<213> ORGANISM: Artificial Sequence
<220> FEATURE:
<223> OTHER INFORMATION: primer HL161 gDicer

<400> SEQUENCE: 124
tccccgcacg caagaagaa                                                 19

<210> SEQ ID NO 125
<211> LENGTH: 18
<212> TYPE: DNA
<213> ORGANISM: Artificial Sequence
<220> FEATURE:
<223> OTHER INFORMATION: primer HL164 gAgo

<400> SEQUENCE: 125
attgccccct acggtgtc                                                  18

<210> SEQ ID NO 126
<211> LENGTH: 18
<212> TYPE: DNA
<213> ORGANISM: Artificial Sequence
<220> FEATURE:
<223> OTHER INFORMATION: primer HL165 gAgo

<400> SEQUENCE: 126
ctctgccggc cttcctac                                                  18

<210> SEQ ID NO 127
<211> LENGTH: 23
<212> TYPE: DNA
<213> ORGANISM: Artificial Sequence
<220> FEATURE:
<223> OTHER INFORMATION: primer HL187 gRdRP

<400> SEQUENCE: 127
```
catgggttgc agtttcttga cga                                              23

<210> SEQ ID NO 128
<211> LENGTH: 24
<212> TYPE: DNA
<213> ORGANISM: Artificial Sequence
<220> FEATURE:
<223> OTHER INFORMATION: primer HL188 gRdRP

<400> SEQUENCE: 128
agccccttat ctgttgcctc cttc                                             24

<210> SEQ ID NO 129
<211> LENGTH: 21
<212> TYPE: DNA
<213> ORGANISM: Artificial Sequence
<220> FEATURE:
<223> OTHER INFORMATION: primer HL 183 CWP1

<400> SEQUENCE: 129
tcgccctgga tgtttcggac a                                                21

<210> SEQ ID NO 130
<211> LENGTH: 17
<212> TYPE: DNA
<213> ORGANISM: Artificial Sequence
<220> FEATURE:
<223> OTHER INFORMATION: primer HL184 CWP1

<400> SEQUENCE: 130
aggcgggtga ggcagta                                                     17

<210> SEQ ID NO 131
<211> LENGTH: 21
<212> TYPE: DNA
<213> ORGANISM: Artificial Sequence
<220> FEATURE:
<223> OTHER INFORMATION: primer HL185 GDH

<400> SEQUENCE: 131
agtggggcgg gtctttactc a                                                21

<210> SEQ ID NO 132
<211> LENGTH: 24
<212> TYPE: DNA
<213> ORGANISM: Artificial Sequence
<220> FEATURE:
<223> OTHER INFORMATION: primer HL186  GDH

<400> SEQUENCE: 132
tgttcgcgcc catctggtag ttct                                             24

<210> SEQ ID NO 133
<211> LENGTH: 23
<212> TYPE: DNA
<213> ORGANISM: Artificial Sequence
<220> FEATURE:
<223> OTHER INFORMATION: primer F RdRP_F

<400> SEQUENCE: 133
tatgttttta ctgatggcgc agg                                              23

<210> SEQ ID NO 134
<211> LENGTH: 23
<212> TYPE: DNA

```
<213> ORGANISM: Artificial Sequence
<220> FEATURE:
<223> OTHER INFORMATION: primer RdRP_F 2

<400> SEQUENCE: 134
tacgtcttta ccgatggcgg agg                                              23

<210> SEQ ID NO 135
<211> LENGTH: 20
<212> TYPE: DNA
<213> ORGANISM: Artificial Sequence
<220> FEATURE:
<223> OTHER INFORMATION: primer RdRP_R

<400> SEQUENCE: 135
tcaccatcca ggtcgctgcc                                                  20

<210> SEQ ID NO 136
<211> LENGTH: 20
<212> TYPE: DNA
<213> ORGANISM: Artificial Sequence
<220> FEATURE:
<223> OTHER INFORMATION: primer RdRP_R 2

<400> SEQUENCE: 136
tcaccgtcca ggtcactgcc                                                  20

<210> SEQ ID NO 137
<211> LENGTH: 20
<212> TYPE: DNA
<213> ORGANISM: Artificial Sequence
<220> FEATURE:
<223> OTHER INFORMATION: primer of sequencing F

<400> SEQUENCE: 137
cttgtgcata gtaaacaaag                                                  20

<210> SEQ ID NO 138
<211> LENGTH: 18
<212> TYPE: DNA
<213> ORGANISM: Artificial Sequence
<220> FEATURE:
<223> OTHER INFORMATION: primer of sequencing R

<400> SEQUENCE: 138
caaatggtcg atgctggg                                                    18

<210> SEQ ID NO 139
<211> LENGTH: 51
<212> TYPE: DNA
<213> ORGANISM: Artificial Sequence
<220> FEATURE:
<223> OTHER INFORMATION: MCSnewSense

<400> SEQUENCE: 139
gattccgggc ccagatctat cgatacgcgt atgcattcgc gagatatctg c               51

<210> SEQ ID NO 140
<211> LENGTH: 52
<212> TYPE: DNA
<213> ORGANISM: Artificial Sequence
<220> FEATURE:
<223> OTHER INFORMATION: MCSnewAntisense

<400> SEQUENCE: 140
gcggccgcag atatctcgcg aatgcatacg cgtatcgata gatctgggcc cg              52
```

<210> SEQ ID NO 141
<211> LENGTH: 28
<212> TYPE: DNA
<213> ORGANISM: Artificial Sequence
<220> FEATURE:
<223> OTHER INFORMATION: primer DAF

<400> SEQUENCE: 141
agttgaaact atcatggttg ctcccgaa                                    28

<210> SEQ ID NO 142
<211> LENGTH: 27
<212> TYPE: DNA
<213> ORGANISM: Artificial Sequence
<220> FEATURE:
<223> OTHER INFORMATION: primer DAR

<400> SEQUENCE: 142
ccaccatggt tgaacgccga atccaac                                     27

<210> SEQ ID NO 143
<211> LENGTH: 31
<212> TYPE: DNA
<213> ORGANISM: Artificial Sequence
<220> FEATURE:
<223> OTHER INFORMATION: primer RAF

<400> SEQUENCE: 143
gcgataggtt gcagttccat gacgttcttg a                                31

<210> SEQ ID NO 144
<211> LENGTH: 29
<212> TYPE: DNA
<213> ORGANISM: Artificial Sequence
<220> FEATURE:
<223> OTHER INFORMATION: primer RAR

<400> SEQUENCE: 144
ccaccatggt cgctacctta gcatcatcc                                   29

<210> SEQ ID NO 145
<211> LENGTH: 5
<212> TYPE: PRT
<213> ORGANISM: Giardia intestinalis

<400> SEQUENCE: 145

Cys Arg Gly Lys Ala
1               5

<210> SEQ ID NO 146
<211> LENGTH: 48
<212> TYPE: PRT
<213> ORGANISM: Artificial Sequence
<220> FEATURE:
<223> OTHER INFORMATION: synthetic multiple antigen peptide
<220> FEATURE:
<221> NAME/KEY: MOD_RES
<222> LOCATION: (48)..(48)
<223> OTHER INFORMATION: bAla

<400> SEQUENCE: 146

Cys Arg Gly Lys Ala Cys Arg Gly Lys Ala Cys Arg Gly Lys Ala Cys
1               5                   10                  15

Arg Gly Lys Ala Cys Arg Gly Lys Ala Cys Arg Gly Lys Ala Cys Arg
            20                  25                  30

```
Gly Lys Ala Cys Arg Gly Lys Ala Lys Lys Lys Lys Lys Lys Lys Ala
     35                  40                  45
```

MODIFIED PROTOZOAN EXPRESSING AT LEAST TWO VARIABLE SURFACE PROTEINS (VSP), A VACCINE COMPRISING IT AND PROCEDURES, USES, AND METHODS THEREOF

This application is the U.S. national phase of International Application No. PCT/IB2009/055470, filed 2 Dec. 2009, which designated the U.S. and claims the benefit of U.S. Application No. 61/119,058, filed 2 Dec. 2008, the entire contents of each of which are hereby incorporated by reference.

The present invention refers to modified protozoa expressing more than one variable surface protein (VSP), a vaccine comprising it, a hybridoma line, a protein-recognizing monoclonal antibody, procedures, uses, and methods thereof. More specifically, it refers to modified parasite protozoa comprising simultaneous surface expression of more than one variable surface protein (VSP). Modified protozoa may also simultaneously express the complete repertoire of variable surface proteins. Protozoa show reduced expression of Dicer, RNA-dependant RNA-polymerase (RdRP) enzymes or both, where the RdRP gene and/or the Dicer gene have been silenced. The protozoan may be any protozoan having an antigenic variation mechanism and the expression may be silenced by molecules regulating this mechanism.

BACKGROUND

The antigenic variation is a clone phenotypical change developed by pathogenic microorganisms involving surface exposed antigenic determinants. These organisms use different mechanisms to change their surface antigen expression, thus being able to maintain a chronic infection under the continuous immune pressure generated by the host (Deitsch, K. W., Moxon, E. R. & Wellems, T. E. Microbiol. Mol. Biol. Rev. 61, 281-293 (1997)). *Giardia lamblia* (also runwayd *Giardia intestinalis* or *Giardia duodenalis*) is one of the most common human intestinal parasites. Protozoan *G. lamblia* also shows antigenic variation (Adam, R. D. Clin. Microbiol. Rev. 14, 447-475 (2001) and Nash, T. E. Phil. Trans. R. Soc. Lond. B 352, 1369-1375 (1997)), in a process that allows the parasite to develop chronic and/or recurrent infections. From a repertoire of about 190 genes codifying variable surface proteins (VSPs), *Giardia* only expresses one VSP on the surface of each parasite at a particular time, but spontaneously switches to a different VSP by an unknown mechanism. In *Giardia*, antigenic variation is responsible for the variable and/or persistent course of some infections, as well as the tendency to multiple infections, and involves a protein family known as VSPs (Adam, R. D. Clin. Microbiol. Rev. 14, 447-475 (2001) and Nash, T. E. Phil. Trans. R. Soc. Lond. B 352, 1369-1375 (1997).

VSPs line the complete trophozoite surface and are the main antigens recognized by the host immune response. VSPs range in size between 30 kDa and 200 kDa; they possess a variable cysteine-rich amino-terminal region and a conserved carboxy-terminal region that includes a hydrophobic transmembrane domain and a short cytosolic tail comprising only 5 amino acids (CRGKA (SEQ ID NO:145)). The parasite genome encodes a repertoire of ~190 genes codifying VSPs (Morrison, H. G. et al. Science 317, 1921-1926 (2007), but only one VSP is expressed at any given time on the surface of each trophozoites. Switching to the expression of another VSP occurs once every 6-13 generations, even in the absence of any immunological pressure (Nash, T. E., Alling, D. W., Merritt, J. W. Jr & Conrad, J. T. Exp. Parasitol. 71, 415-421 (1990). Similarly to the rest of *G. lamblia* genes, the VSPs codifying genes have no introns and their upstream regions are relatively short and have been found to have limited or no sequence conservation. Moreover, there are no typical eukaryotic promoters present in these regions. The non-translated 3' regions of messenger RNA including *Giardia* VSPs genes also tend to be short, typically 0-30 nucleotides long. So far, neither gene-rearrangement processes nor promoter-dependent switch-on/switch-off mechanisms have been demonstrated to be involved in *Giardia*'s antigenic switching (Adam, R. D. Clin. Microbiol. Rev. 14, 447-475 (2001); Nash, T. E. Phil. Trans. R. Soc. Lond. B 352, 1369-1375 (1997) and Nash, T. E., Ailing, D. W., Merritt, J. W. Jr & Conrad, J. T. Exp. Parasitol. 71, 415-421 (1990).

BRIEF DESCRIPTION OF THE INVENTION

Modified parasite protozoa comprising simultaneous surface expression of more than one variable surface protein (VSP) are provided. In a preferred embodiment the protozoa comprise the simultaneous surface expression of the complete repertoire of variable surface proteins. Protozoa show a reduced expression of the Dicer, RNA-dependant RNA-polymerase (RdRP) or both, where the RdRP gene or the Dicer gene has been silenced, or a mixture thereof. The protozoan may be any protozoa showing an antigenic variation mechanism, where its antigenic variation mechanism may be unregulated by silencing any of its components.

A vaccine against infections produced by protozoa comprising at least a modified protozoan expressing on its surface at least two variable surface proteins (VSP) is provided. In a preferred embodiment the protozoa comprise simultaneous expression of the complete repertoire of variable surface proteins on its surface. Protozoa show reduced expression of the Dicer, RNA-dependant RNA-polymerase (RdRP) enzymes or both, where the RdRP gene or the Dicer gene has been silenced, or a mixture thereof. The protozoan may be any protozoan showing an antigenic variation mechanism. The vaccine may also comprise excipients and/or adjuvants.

A procedure to purify the complete repertoire of protozoan variable surface proteins (VSP) is provided, comprising:

a) linking an antibody recognizing the VSP CRKGA amino acid sequence of to a solid support;

b) contacting the solid support to protozoa; and c) separating the complete repertoire of variable surface proteins (VSP). The protozoa may be a mixture of wild protozoa clones, where each clone expresses a different variable surface protein or may be a clone expressing the complete VSPs repertoire A vaccine comprising more than one protozoan variable surface protein is provided, where each of said proteins is different; and excipients and/or adjuvants. In a preferred embodiment the vaccine comprises the complete repertoire of protozoan variable surface proteins, where each of said proteins is different.

An immunization method comprising administering to a mammal an amount of a vaccine comprising modified protozoan expressing at least two variable surface proteins (VSP) or expressing simultaneously the complete repertoire of protozoan VSPs is provided. The method is applied in order to immunize a mammal against infections produced by protozoa, where said protozoa have an antigenic variation mechanism.

In addition, an immunization method comprising administering to a mammal an amount of a vaccine comprising a combination of protozoan variable surface proteins is provided, where the combination of variable surface proteins is isolated from a modified protozoan comprising silenced RdRP genes, Dicer genes or both. The method is applied to immunize a mammal against infections produced by protozoa, where said protozoa have an antigenic variation mechanism. In an embodiment, the administered vaccine dose comprises between 50 and 500 μg of protozoan variable surface proteins.

A nucleotide sequence is provided, wherein said sequence may be chosen between anyone of sequences SEQ ID No 1 a SEQ ID No 112, wherein said sequences are ARNdc.

The use of at least a sequence chosen between anyone of sequences SEQ ID No 1 a SEQ ID No 112 is provided to silence the RdRP gene or to silence the Dicer gene.

c: to verify if *Giardia* VSP transcript silencing implied VSP antisense ARN, these molecules were searched for in ARN preparations isolated from trophozoites expressing a unique VSP, RT-PCR were carried out with the same VSP primer combinations previously used in the genomic DNA but using sense primers during the reverse transcription reaction (RT), sense primers (S1 to S4) are shown on top, runways (a) to (h) indicate primer combinations used in each PCR reaction: (a) S1-R1, (b) S2-R1, (c) S3-R1, (d) S4-R1, (e) S1-R2, (f) S2-R2, (g) S3-R2, and (h) S4-R2; in addition, negative controls without reverse transcriptase (RT-) are shown. In these conditions thirty eight amplified products were isolated, cloned and sequenced, demonstrating antisense codifying VSPs, twelve of these products (marked 1 to 12 in target) were also used as probes in a genome library, which allowed to obtain the complete sequence of new VSP genes (VSPAS1-VSPAS12, GenBank access numbers AY143130-AY142141), indicating functional targets of VSP genes antisense transcripts.

Figure 3:
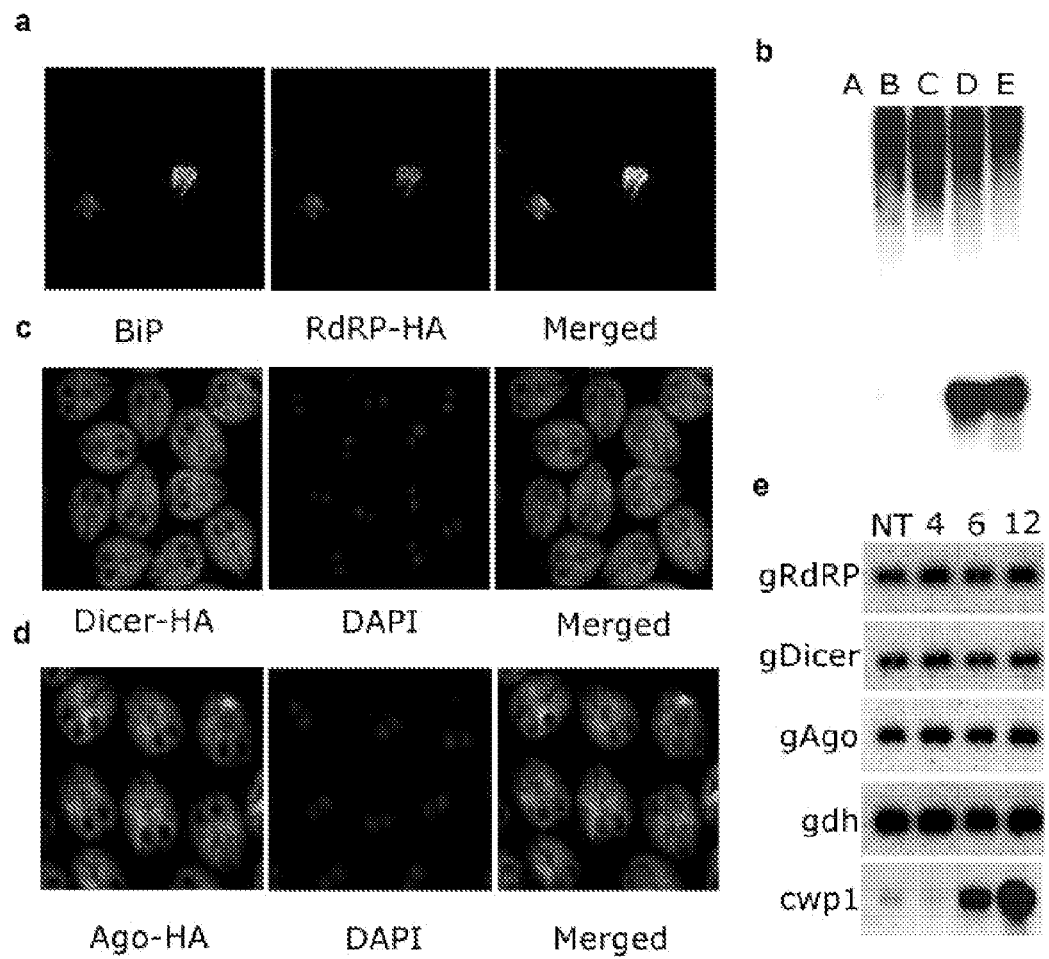

FIG. 3 shows a: immunolocation of the gRdRP version labeled with a HA epitope expressed in WB9B10 clone trophozoites, the la enzyme (in red) is localized in a region surrounding both parasite nuclei; this region mainly refers to rough endoplasmic reticulum (yellow) as seen by co-immunolocation with chaperone ER-BiP (Mab 9C9, in green); b: RdRP activity, wherein different RNA substrate combinations were used (A, B, and D; vsp9B10 and vsp1267; C and E; vsp9B10, vsp1267, and vspH7), in absence (A-C) or in presence of primer R1 (D) or R2 (E), A is a control without purified RdRP. c: immunolocation of a gDicer version labeled with a HA epitope expressed in WB9B10 clone trophozoites, the enzyme (in green) localizes in the cell cytoplasm, nuclei are stained with DAPI (blur); d: immunolocation of a gAgo version signaled with a HA epitope, which is expressed in WB9B10 clone trophozoites, the enzyme (in green) is localized in the cell cytoplasm, nuclei are stained with DAPI (blue); e: Northern blot with probes for gRdRP, gAgo, gDicer, GDH and CWP1 on total RNA extracted from WB9B10 clone trophozoites induced to cyst formation during 4, 6, or 12 h, and trophozoites maintained in a normal growth medium (NT) for 12 h., results show the constitutive expression of these PTGS components (post transcriptional gene silencing).

Figure 4:
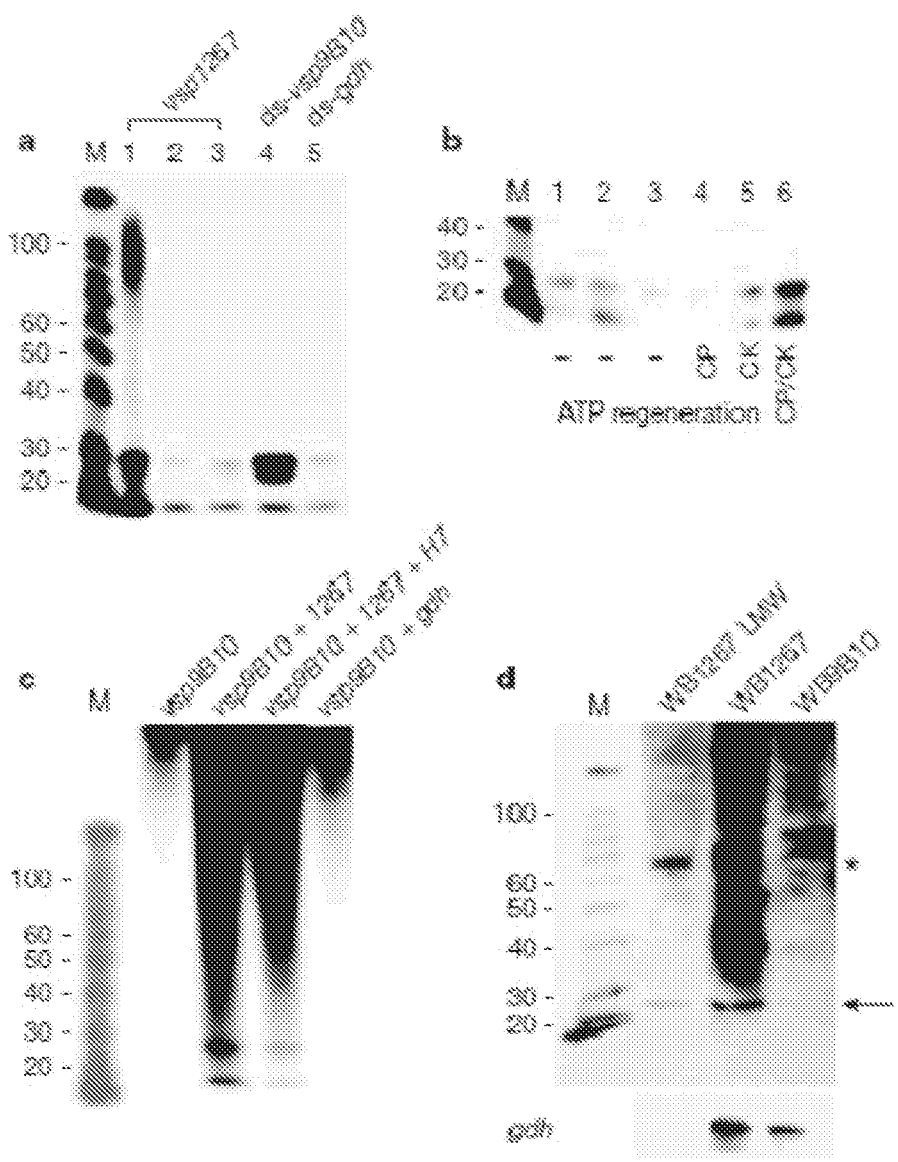

FIG. 4 shows Dicer activity and detection of small VSP RNA in *Giardia*. a: generation of small RNAs from dsRNA by *Giardia* extract demonstrating a Dicer-type activity. For vsp1267dsRNA, both strands (runway 1), sense RNA strand only (runway 2) or antisense only (runway 3) were radioactively labeled. For vsp9B10 and gdh, both strands were labeled. Double-strand RNAs were incubated with a *Giardia* extract from WB9B10 clone at 37° C. for 1 h; then, total RNA was isolated and used for electrophoresis. In all cases, small RNA were obtained; b: effect of the presence of ATP in dsRNA processing by *Giardia*, runways 1 and 2 show non-treated controls: incubation of vsp1267 dsRNA with *Giardia* cytoplamic lysates without wasting ATP (1 h and 3 h incubation, respectively), ATP reduction by addition of 2 mM glucose and 0.1 U μL$^{-1}$ of hexo-kinase (runway 3). ATP regeneration using phosphocreatine (CP, runway 4), creatine kinase (CK, runway 5), or both (runway 6); c: generation of small RNAs by incubation of VSP riboprobes with extracts form *Giardia* WB9B10 clone. One, two or three different VSP RNAm (vsp9B10, vsp1267, vspH7) were blended with the *Giardia* extracts. Formation of small RNAs occurred in the presence of more than one transcript. gdh was used as non-related gene control. RNA size markers in nucleotides are on the left-hand side; d: total WB9B10 clone RNA and of WB1267 clone trophozoites, as well as low molecular weight WB1267 clone RNA (LMW-low molecular weight) were subjected to electrophoresis, blotted and hybridized using partially digested vsp9B10 RNA probes transcribed in-vitro. No small RNA was found in the WB9B10 clone; in contrast, small vsp9B10 RNAs were present in the WB1267 clone (arrow), which does not express VSP9B0. Curiously, 70-nucleotides long RNAs (asterisk) were found which could represent partially digested RNAm.

Figure 5:
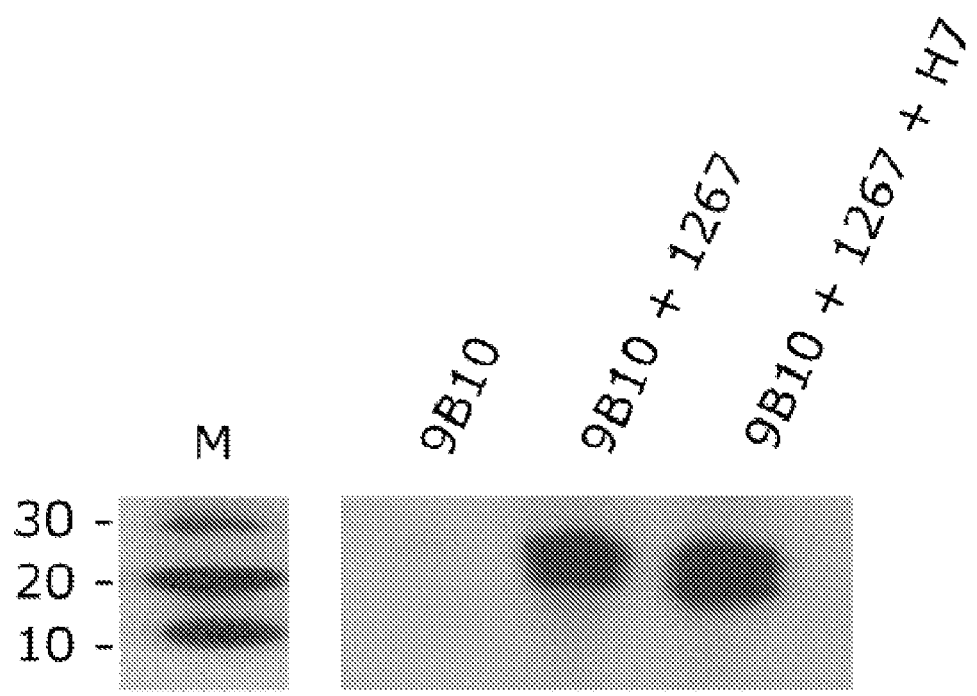

FIG. 5 shows generation of small RNAs by incubation of VSP riboprobes with Giardia WB1267 clone extracts; one, two, or three RNAm of different VSP (vsp9B10, vsp1267, vspH7) were blended and confronted to the Giardia trophozoite extracts, small [32P] marked RNA were generated when more than one transcript was present, RNA size markers in nucleotides are on the left-hand side.

Figure 6:
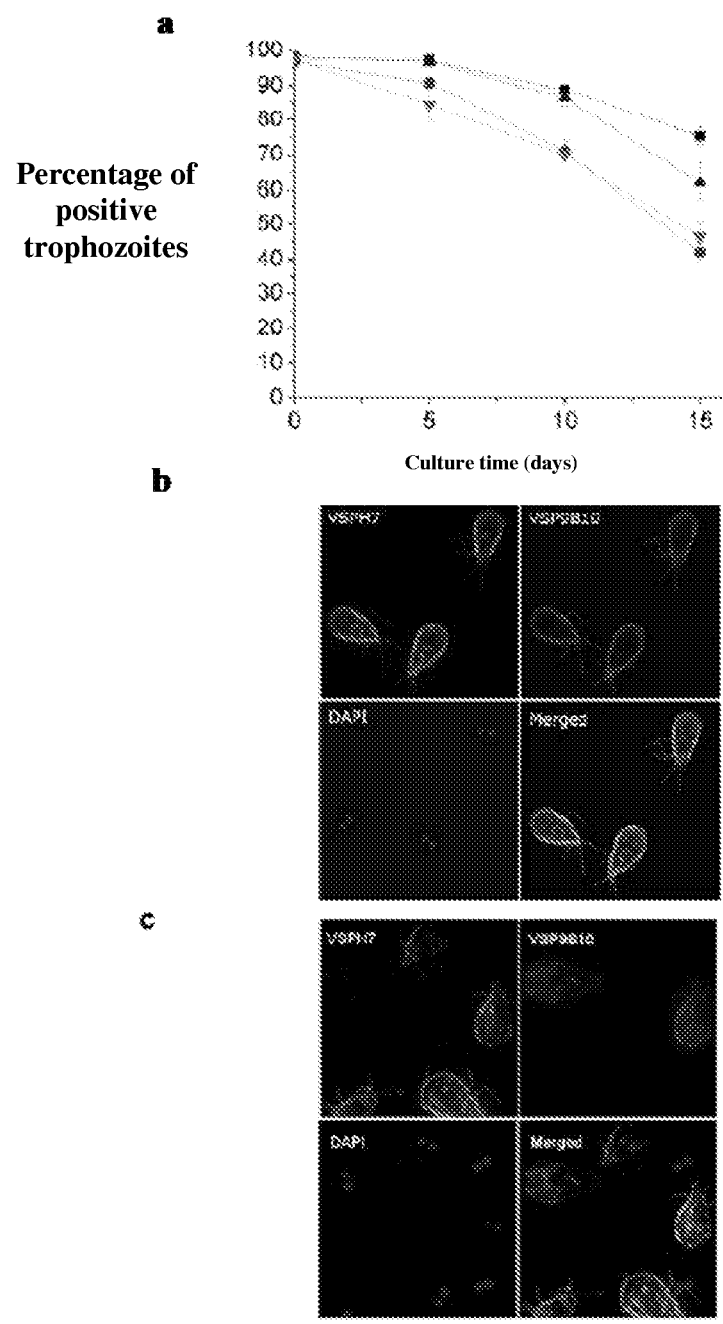
Figure 7:
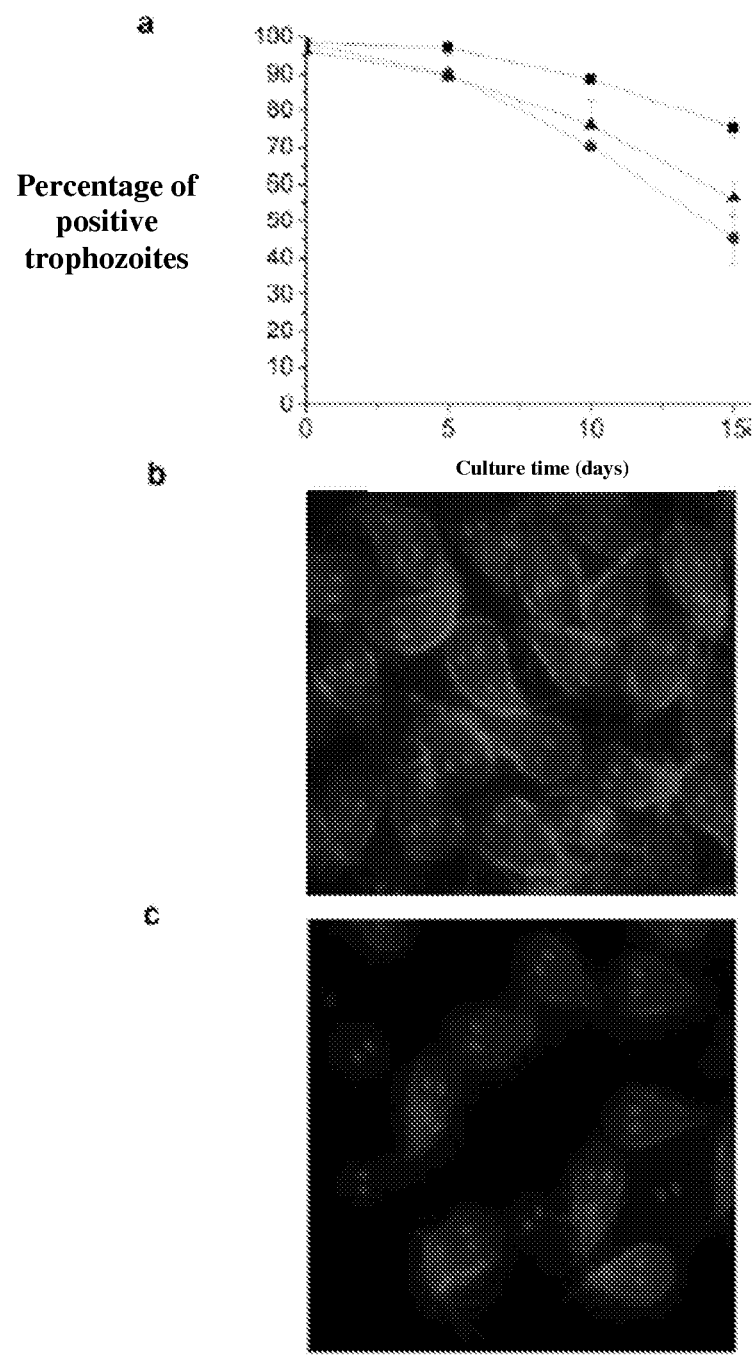

FIG. 6 shows an antigenic commutation in WB9B10 trophozoites overexpressing VSPH7. a: WB9B10 clone trophozoites were transfected with pTubCWP1.Pac vector or with pTubH7.Pac vector, directing CWP1 or VSPH7 expression under control of the α-tubulin promotor, with controls from trophozoites from the GS strain expressing VSP H7 transfected with control vector (pTubCWP1.Pac) indicated by inverted triangles, squares showing WB9B10 trophozoites transfected with control vector, VSP 9B10 expression diminishes with time due to spontaneous exchange of the surface proteins, with WB9B10 trophozoites constitutively expressing vspH7 showing that the VSP9B10 (circles) or VSPH7 (triangles) expression diminished faster than the respective control. Results represent average percentage of three independent experiments±SD. b: Representative image of WB9B10 trophozoites expressing VSPH7 on time 0, all cells simultaneously expressing VSP9B10 and VSPH7 on its surface; c: representative image of WB9B10 trophozoites expressing VSPH7 after 15 days culture, some cells express VSP9B10 and VSPH7 on its surface, others VSP9B10 or VSPH7 only and other neither one; nuclei were marked with DAPI in blue;

FIG. 7 shows antigenic commutation in WB9B10 trophozoites expressing vsp9B10 antisense fragments. a: WB9B10 clone trophozoites were transfected with vector pTubCWP1.Pac vector (squares) or pTubPac vector including antisense sequences of the mean portion media of vsp9B10 gene 5'(circle) or 3' (triangle); results represent average value of three independent experiments±SD and indicate that the amount of VSP 9B10 positive trophozoites diminish faster than control; b: representative image of WB9B10 trophozoites transfected with a different VSP gene, with all cells expressing VSP9B10 on its surface; c: representative image of WB9B10 trophozoites expressing the antisense fragment 3' of vsp9B10 after 15 days culture, VSP9B10 is present in about 50% of population; nuclei were marked with DAPI in blue.

Figure 8:
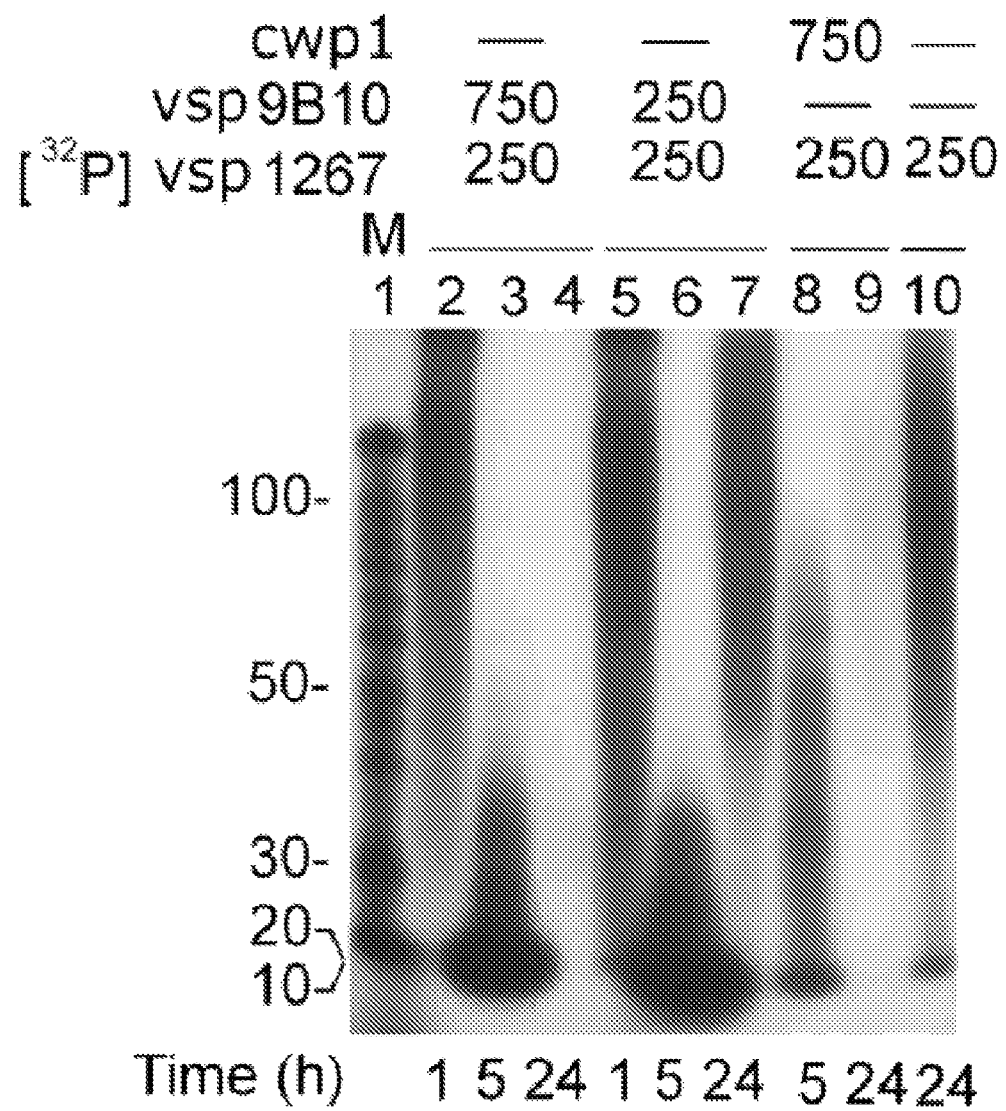
Figure 9:
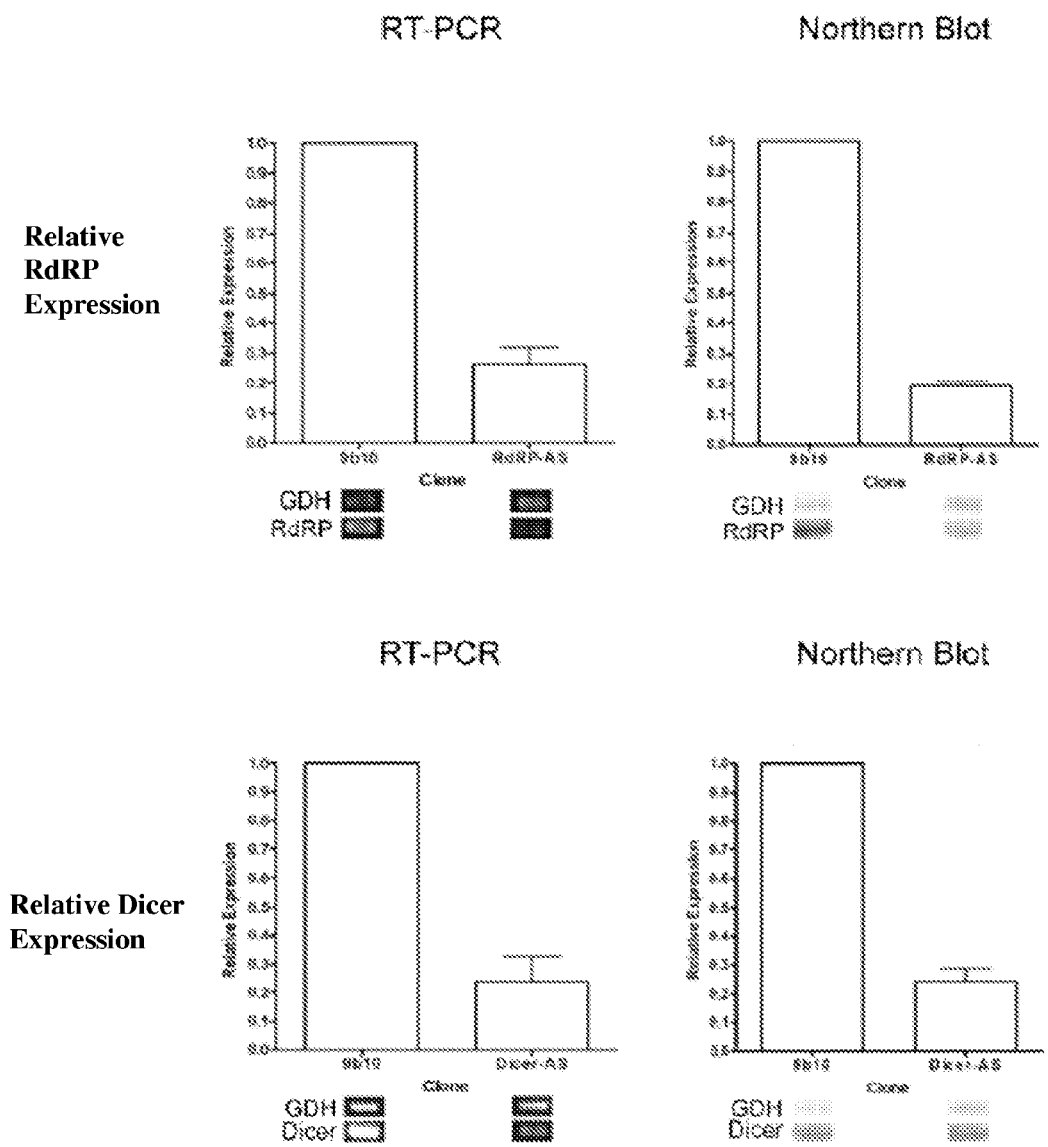

FIG. 8 shows that variations in concentration of different transcripts may determine which one evades the silencing system. VSP codifying 1267, vsp9B10, and cwp1 genes were cloned in pGEM-T-easy vector and transcribed in vitro in the presence or absence of 32P-UTP, different concentrations of non-marked vsp9B10 and CWP1 transcripts were generated during different periods of time with WB1267 cytoplasmic extracts containing a fixed concentration of vsp1267 radioactively marked RNA, runway 1: marker of dozens of nucleotides (Decade-Ambion), runways 2, 3 and 4: incubation of 750 ng vsp9B10 and 250 ng vsp1267 (ratio 3:1), 1, 5 and 24 h, respectively, runways 5, 6 and 7: incubation equal amounts of vsp9B10 and vsp1267 (250 ng each; ratio 1:1), 1, 5 and 24 h, respectively, runways 8 and 9: incubation of 750 ng CWP1 and 250 ng vsp1267, 5 and 24 h, respectively, runway 10: incubation of 250 ng vsp1267 transcript, in short incubation periods (1 h) there is little vsp1267 degradation in WB1267 clone, independently of the amount of vsp9B10 added to the mixture (runways 2 and 5). In contrast, after longer incubations (5 hs) the appearance of small radiolabeled vsp1267 RNAs increases by the presence of vsp9B10 (compare runway 10 with runways 3, 6 and 8), the presence of CWP1 transcripts (not related) has no effect, including at high concentration (runway 8). At 24 hs incubation, most radiolabeled transcripts are totally broken down;

FIG. 9 shows the results of silencing the Dicer and RdRP gene in Giardia trophozoites, wherein Giardia Dicer-AS and RdRP-AS clones present a reduction of RNA messenger levels of between 65% and 75% in comparison with non-transfected WB9B10 trophozoites measured by densitometry assays of bands obtained by RT-PCR and Northern blot performed five times, where results represent average value±s.d.

Figure 10:
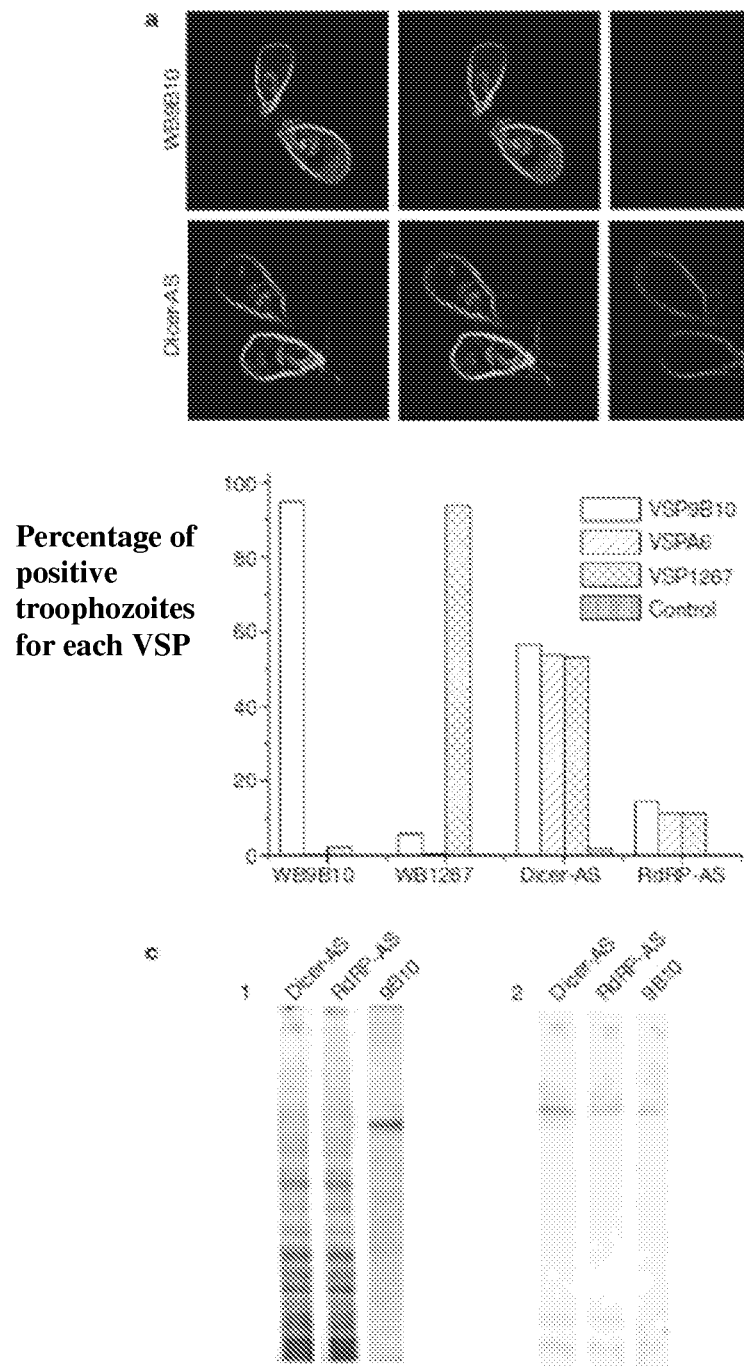

FIG. 10 shows the expression of differents VSPs in transgenic Giardia trophozoites with silenced RdRP and Dicer enzymes, a: direct of immunofluorescence assays in Dicer-AS transfected trophozoites (lower panel) or empty vector (top panel) using TRITC conjugated to 5C1 monoclonal antibody (VSP1267; right panel) and FITC conjugated to 9B10 monoclonal antibody (VSP9B10; left panel), when Dicer expression in Giardia was silenced, trophozoites expressing surface VSP9B10 also expressed VSP1267 (fused image; central panel); b: percentage of Giardia trophozoites expressing a particular VSP, as determined by flow cytometry assays using specific monoclonal antibodies (VSP9B10, 9B10 monoclonal antibody; VSP1267, 5C1 monoclonal antibody; VSPA6, 6E7 monoclonal antibody) in 9B10, 1267, clones and with transfected cells with antisense constructions for Giardia RdRP (RdRP-AS) or Dicer (Dicer-AS), as negative control were used anti-rat goat immunoglobulins; c: Western blot test of protein extracts of wild type WB9B10 and trophozoites WB9B10 wherein Dicer gene has been knocked out, after electrophoresis and transference to nitrocellulose, filters were hybridized with: (1) 12F1 monoclonal antibody G3 clone of the invention (generated against the CRGKA preserved domain in all VSPs) or (2) 9B10 monoclonal antibodies (specific for VSP9B10).

Figure 11:
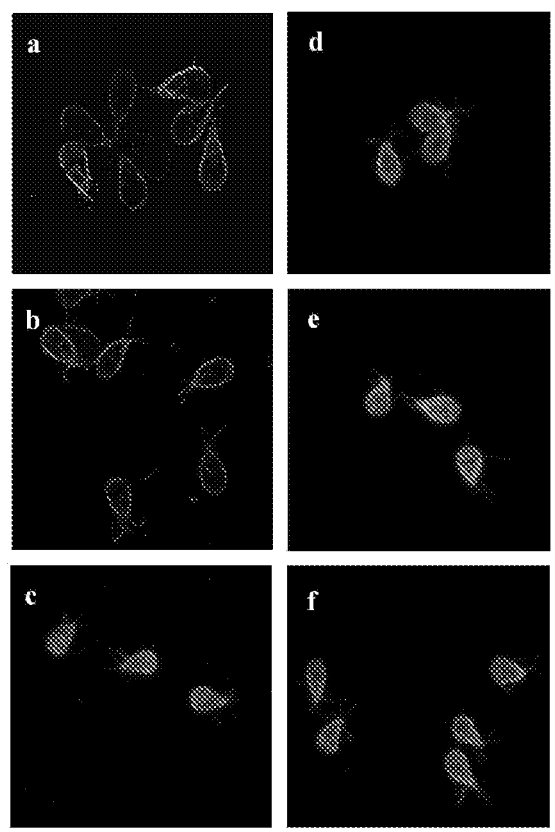

FIG. 11 shows the expression of VSPs in wild type Giardia clones and in Giardia modified with deregulation of antigenic variation; confocal immunofluorescence images of trophozoites are shown, where Dicer (a) or RdRP (b) have been silenced and representative images of indirect immunofluorescence assays using anti-VSP monoclonal antibodies (green) un contrast with DAPI (blue), WB9B10 (d), WB1267 (e), and GS/M-H7 (f), and (c) immunofluorescence image of an isolated non-cloned WB population stained with anti-CRGKA 12F1 monoclonal antibody of the invention (green) and counterstained with DAPI (blue).

Figure 12:
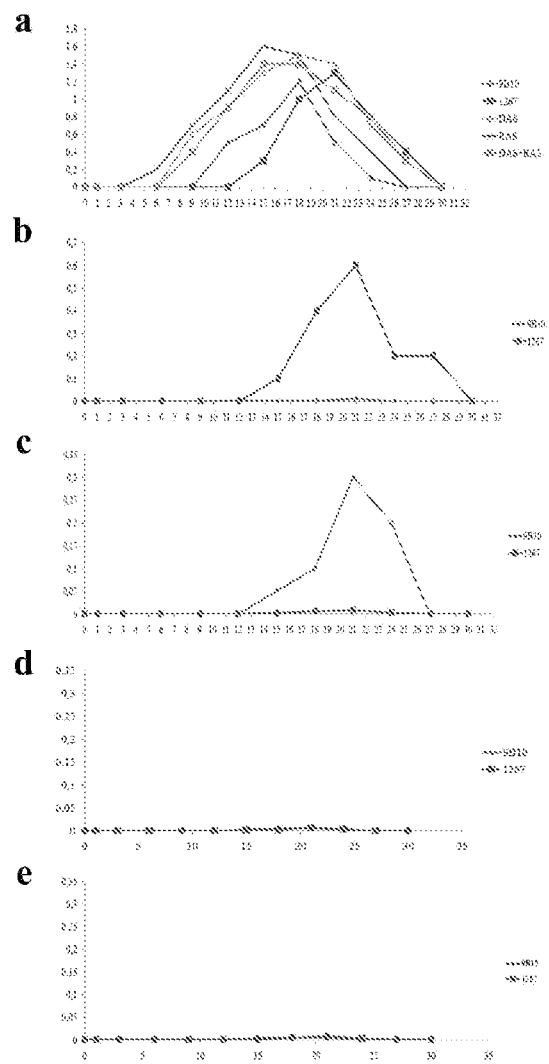

FIG. 12 shows detection and quantification of Giardia cysts in deposition samples from gerbils infected with different populations of wild type and transgenic trofozitos, and challenged with WB9B10 and WB1267. (a) Gerbils initially infected with clone populations of WB9B10, WB1267, or transgenic trophozoites silenced for the expression of Dicer (DAS) or RdRP (RAS) and mixtures 1:1 of both. (b-e) Gerbils previously infected with Giardia WB9B10 (b), WB1267 (c), DAS (d) and RAS (e) were challenged two months after primary infection with clone populations of WB9B10 and WB1267; the amount of cyst released by the animals were counted. Figures represent el mean value of five different experiments;

Figure 13:
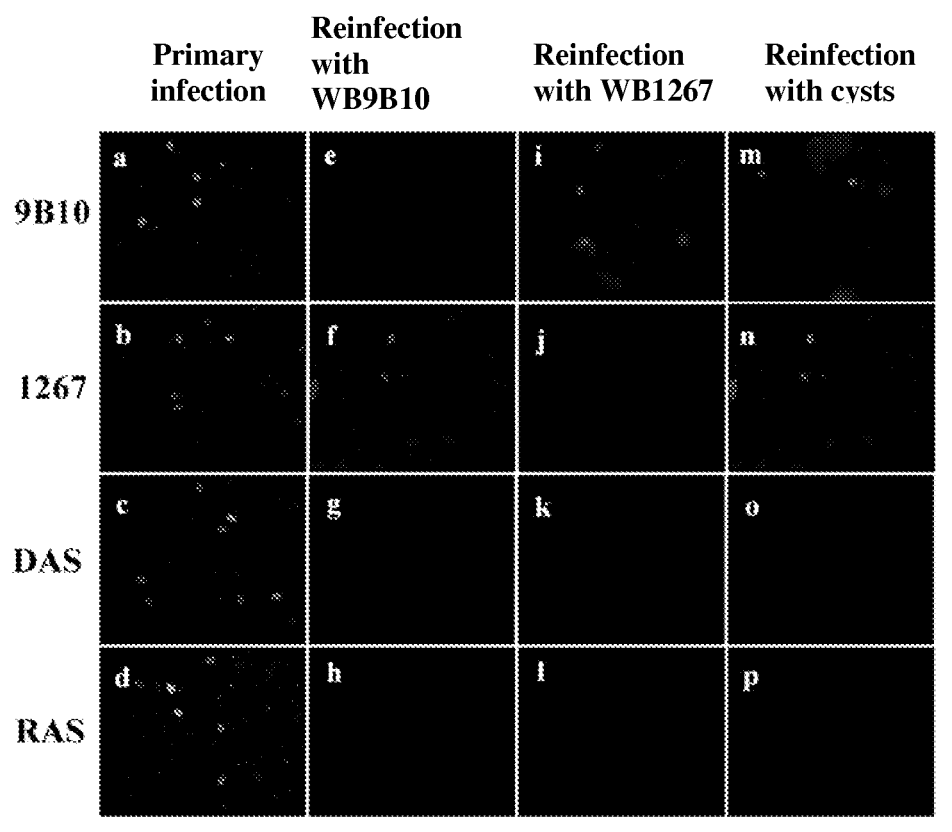

FIG. 13 shows the results of the challenge of gerbils with trophozoites expressing a particular VSP continuing the primary infection with *Giardia* trophozoites expressing complete repertoire of VSPs. Gerbils previously infected with WB9B10, WB1267, DAS, or RAS clones (a-d) were challenged with populations of WB9B10 (e-h), WB1267 clones (i-1), or purified cysts (m-p). The figure shows representative images of immunofluorescence assays in gerbil feces using monoclonal antibodies conjugated with anti-CWP2 FITC (green).

Figure 14:
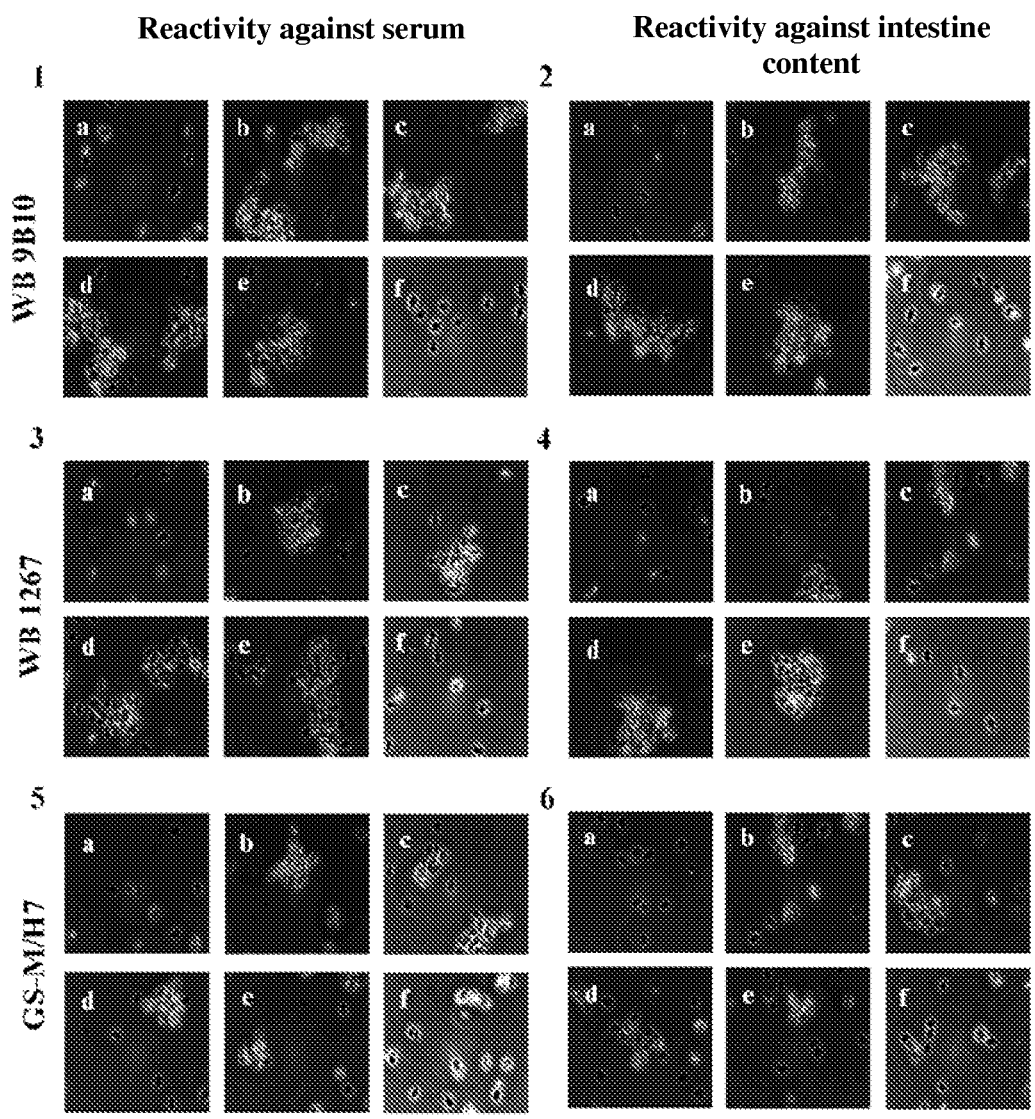

FIG. 14 shows that serum and intestine content of gerbils infected with transgenic trophozoites expressing the complete repertoire of VSPs are capable of agglutinating different *Giardia* clones in vitro. Representative images are shown of phase contrast microscopy of WB9B10 (1-2), WB1267 (3-4), and GS/M H7 clones (5-6) challenged with serum (1b, 3f, and 5f) or intestinal content (2b, 4f, and 6f) of animals infected with WB9B10 clones; serum (2b and 1f), or intestinal content (3b and 2f) of animals infected with WB1267 clones; serum or intestinal content of animals infected with GS/M-H7 clones (5b and 6b); Mab specific for VSP9B10 (1c and 2c), Mab for VSP1267 (3c and 4c), Mab for VSPH7 (5c and 6c), serum of non-infected animals (1a, 2a, 3a, 4a, 5a, and 6a), serum of animals infected with knocked DAS (1d, 2d, 3d, 4d, 5d, and 6d), and serum of animals infected with RAS (1e, 2e, 3e, 4e, 5e, and 6e).

Figure 15:
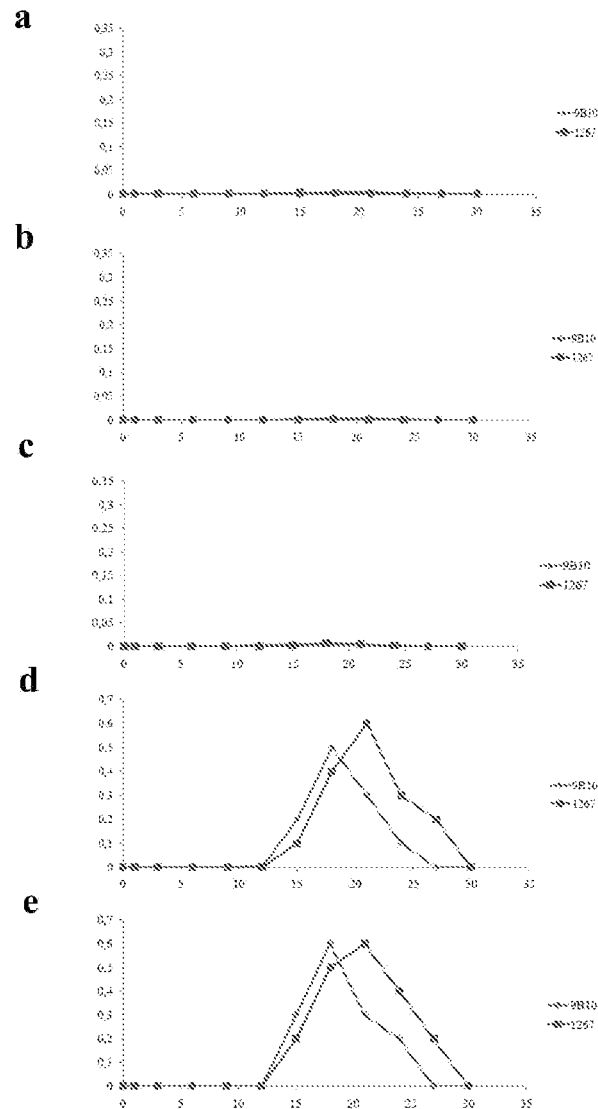
Figure 16:
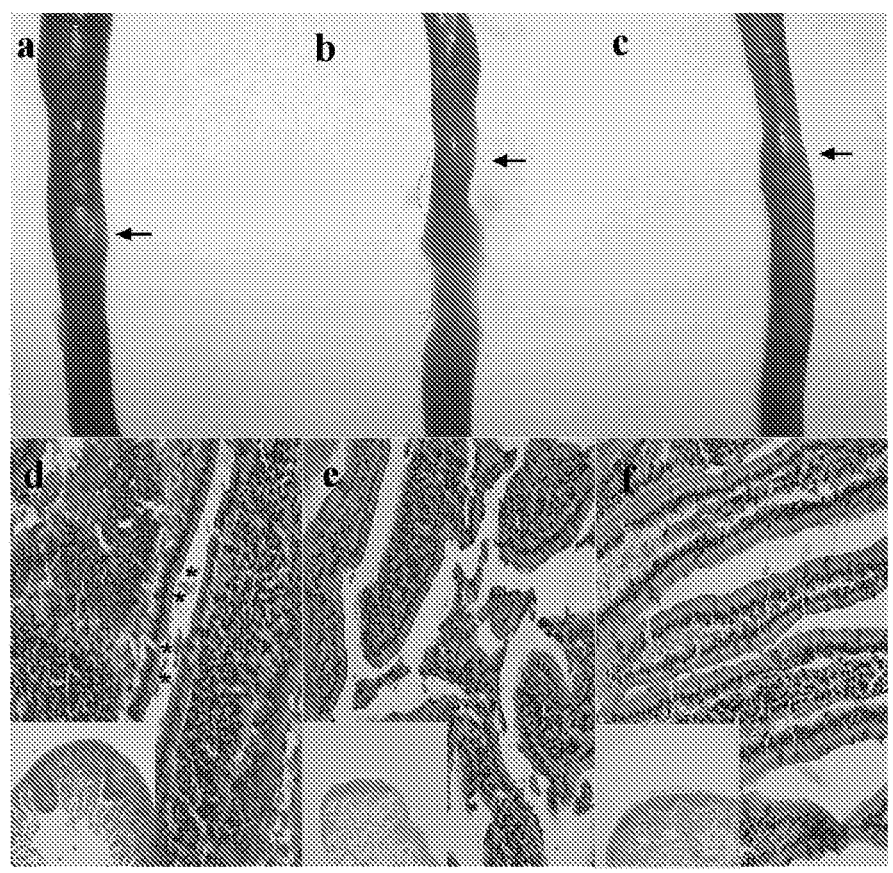

FIG. 15 shows detection and quantification of *Giardia* cysts in feces samples of gerbils previously immunized with purified VSPs from different clone populations of wild type and/or transgenic *Giardia* trophozoites of the invention. Feces pf immunized gerbils were monitored daily for a month using anti-CWP2 monoclonal antibodies to verify cyst release. Gerbils were infected with clone populations of WB9B10 or WB1267 trophozoites. Immunizations were carried out using purified VSPs from transgenic trophozoites DAS, RAS of the invention (and mixtures thereof); the animals were previously immunized with purified DAS (a), RAS (b) VSPs, or a mixture thereof (c); these animals were protected against subsequent infections by WB9B10 or WB1267 clones, control animals (d) or those immunized with intracellular protein (e) were not protected against subsequent infections. The figures represent mean valor of 5 independent experiments;

FIG. 16 shows photographs of gerbil small intestine morphology during the infection and the challenge; top panel shows small intestine of experimental animals: (a) gerbil intestine during primary infection with trophozoites expressing complete repertoire of VSPs (DAS) 15 days after inoculation; an increase of size in Peyer patches is observed (arrows) in comparison with control animals (b). (c) is the intestine during the challenge of gerbils immunized with purified VSPs of DAS trophozoites; lower panel shows experimental animals small intestine microscopic examination: (d) infected gerbils show enlargement of Peyer patches and moderate infiltrative inflammation in mucosa and submucosa. Some *Giardia* trophozoites were seen in the intestine lumen (asterisks; 400×); (e) are non-infected control/no vaccinated gerbils (400×); (f) are vaccinated gerbils showing histologically normal intestinal mucosa (400×), insertions show a general small intestine morphology at 250×.

DETAILED DESCRIPTION

In the present application, trophozoite means a cell of a particular stage of a unicellular parasite, for example of a protozoan. To the effects of the present application, it is understood that the terms trophozoite, parasite, parasite cell, or protozoan have the same meaning and are interchangeable.

In the present application, the transgenic or modified parasite, trophozoite or protozoan of the invention may be a protozoan wherein the Dicer gene or the RdRP gene, or a mixture of transgenic protozoa thereof, have been silenced. These protozoa and interchangeably known in the present application as transgenic, transfected, or modified trophozoites, protozoa or parasites. When silenced, the trophozoite or protozoan Dicer gene of the invention may also be known as Dicer-AS or DAS. When silenced, the trophozoite or protozoan RdRP gene of the invention may also be known as RdRP-AS or RAS. When using a mixture of transgenic trophozoites or protozoa, they may be known as Dicer-AS+RdRP-AS ó DAS+RAS.

In the present application, trophozoites or protozoa expressing complete repertoire of variable surface proteins may be any protozoan parasite or pathogen wherein the antigenic variation mechanism has been deactivated.

It is shown that VSPs expression regulation in *Giardia* includes a system comprising RNA-dependant RNA-polymerase, Dicer and Argonaute, components of the RNA interference machinery. Clones expressing a single surface antigen (protein) in surface, efficiently transcribe several VSP codifying genes, but only accumulate transcripts encoding the VSP to be expressed in the cell surface.

Detection of antisense RNAs corresponding to the silenced VSP genes and small RNAs from the silenced proteins silenciadas but not for the expressed VSP imply a RNA interference pathway in the antigenic variation regulation. Clearly, the silencing of Dicer enzyme and RNA-dependent-RNA polymerase leads to a change from single to multiple VSP expression in individual parasites.

Nuclear run assays were performed to determine if the VSP expression regulation is controlled at the transcriptional or post-transcriptional level. Then the existence of RNA was studied in trophozoites, at sense and antisense, codifying VSP by the reverse transcription polymerase chain reaction (RT-PCR) and for the activity of enzymes involved in the synthesis and degradation of double-stranded (dsRNA) in higher eukaryotes, such as RNA-dependent RNA polymerase (RdRP), Dicer and Argonaute. The characterization involved cloning and expressing these genes as well as the analysis of small RNAs generated from VSPs codifying dsRNAs. Additionally, expression of different VSPs was evaluated after silencing the components of the *Giardia* RNA interference (RNAi) pathway.

Disruption of the antigenic variation mechanisms to generate cells expressing complete repertoire of variable surface proteins in pathogen organisms has not been described yet. The complete repertoire expression of surface proteins in pathogenic organisms to generate parasites which may be used as vaccines, or complete repertoire purification of variable surface proteins for immunoprophylaxis of the diseases caused by these pathogens has not been possible yet.

Figure 1:
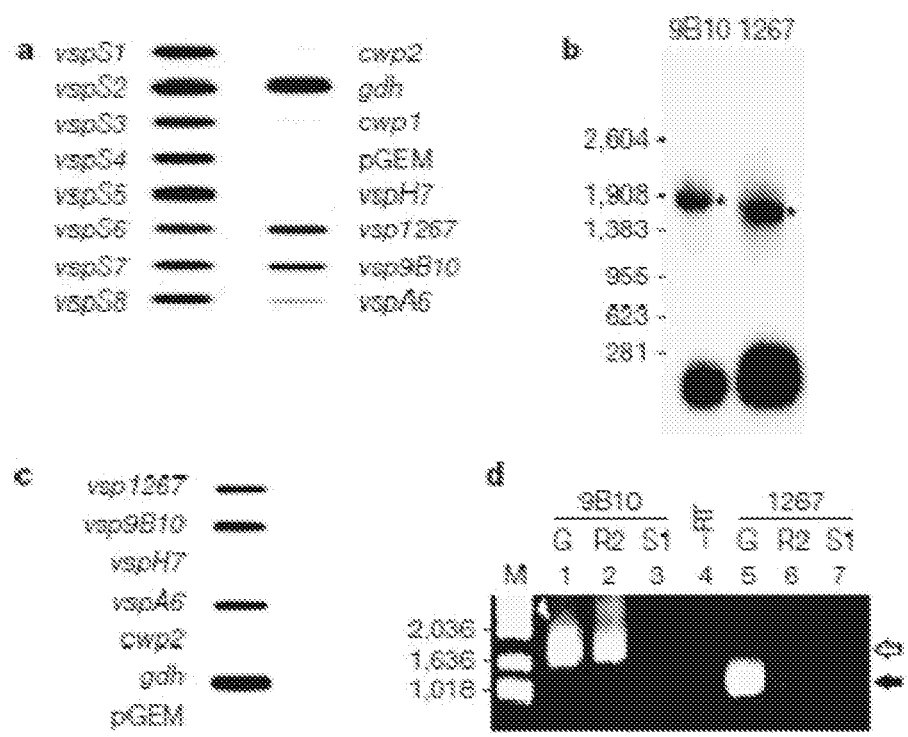
FIG. 1 shows that several VSP genes in *Giardia* are simultaneously transcribed; a: nuclear run-on assay using recently isolated *Giardia* nuclei induced to transcribe in vitro in the presence of [32P] UTP; b: Northern blot test of total RNA extracted from clones WB9B10 and WB1267 using a probe comprising the preserved region present in all VSPs; c: sense and antisense transcripts (vsp9B10, vsp1267, vspA6, vspH7, cwp2 and GDH) generated in vitro, were blotted and hybridized with the assay products of nuclear run on in the same conditions as FIG. 1a; d: Comparison between PCR products generated from clone WB9B10 trophozoites with specific primers (9B10F/9B10R and 1267F/1267R) on the genomic DNA (runways 1 and 5), or cDNA generated either with reverse probe R2 (runways 2 and 6) or sense probe S1 (runways 3 and 7), runway 4 is a reaction control without RT, the white arrow indicates the vsp9B10 fragment, which is present in a genomic DNA and in sense cDNA but not in antisense cDNA, the black arrow indicates the vsp1267 fragment present in genomic DNA, in sense cDNA and in antisense cDNA. M means molecular marker.

Transcription of VSPs in *Giardia*:

Transcription of VSP genes was analyzed by nuclear run-on assays using RNA isolated from nuclei from WB9B10 clone trophozoites (FIG. 1a); said clone expresses only VSP9B10 (GenBank accession number AAK97086) on its surface. The results indicate that most of genes codifying VSPs were simultaneously transcribed. In contrast, when total RNAs extracted from two different *Giardia* clones (WB9B10 and WB1267) were incubated with an oligonucleotide used as probe corresponding to the conserved 3' end of VSP genes, only one transcript of the molecular size corresponding to the VSP expressed on the surface of these clones was detected (FIG. 1b). Additionally, very low-molecular-weight bands, suspected to be degradation products, were seen. Accumulation of only one VSP transcript was observed in different Giardia clones using VSP-specific probes (see Nash, T. E. Phil. Trans. R. Soc. Lond. B 352, 1369-1375 (1997). This demonstrates that only one VSP transcript accumulates, where more than one VSP is transcribed in the parasite nucleus.

Figure 2:
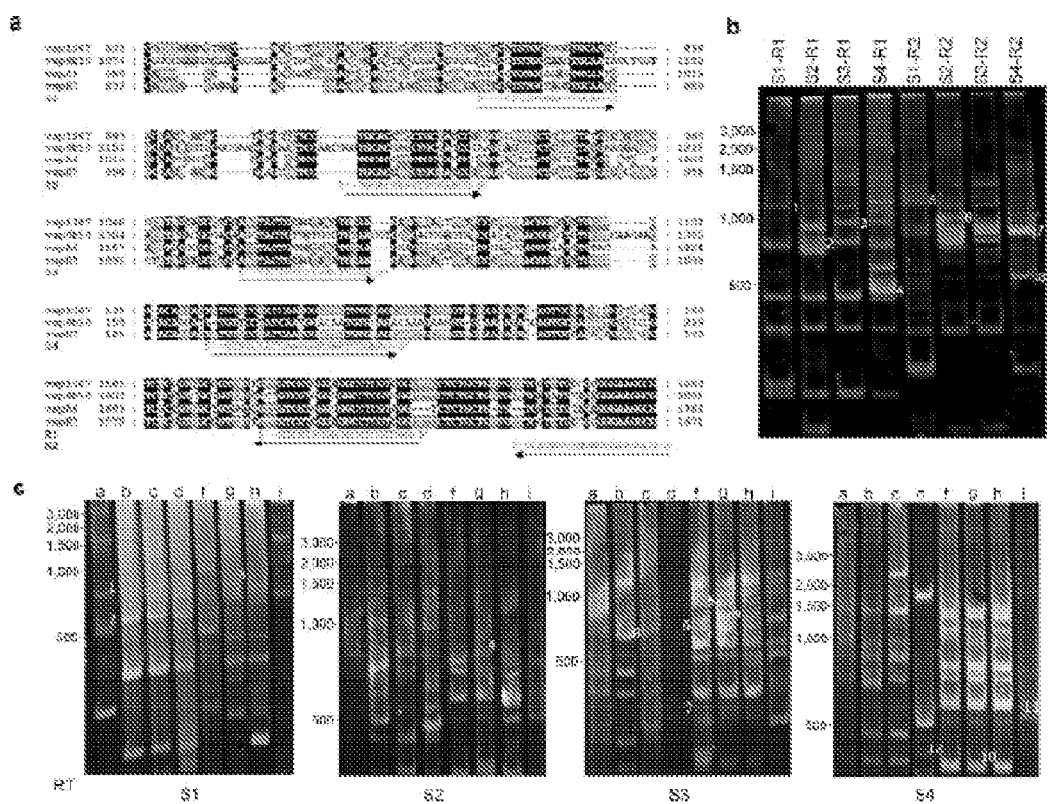
FIG. 2 shows the new tools to study antigenic variation in *G. lamblia*. a: Suitable oligonucleotides to be amplified by PCR to a great amount of VSP codifying genes were generated; sequences of four *G. lamblia* VSPs isolated from (VSP1267, VSP9B10, and VSPA6) and GS (VSPH7) were selected, these four VSP sequences were aligned and the four preserved regions were used to design primers; the arrows below oligonucleotide sequences denote sequences were generic VSP primers (S1-S4 and R1-R2) were designed; b: combination of four sense primers (S1-S4) and dos reverse primers (R1, R2) was used in PCR test of genomic DNA from *Giardia* WB9B10 clone, which only expresses VSP9B10 on its surface, several DNA fragments were amplified independently of the primer combinations used and fifty-nine main products of these reactions were isolated, cloned and sequenced, revealing that they all codified VSP fragments, several of these products (labeled 1 to 8 in white) were subsequently used as probes for the scrutiny of a genomic DNA library, which allowed to identify ORFs (open reading frameworks) codifying new proteins with *Giardia* VSP typical features (VSPS1-S8, GenBank access numbers: AY142122 to AY142129), size markers in nt (nucleotides) are shown at the left-hand side.

Post-transcriptional gene silencing in Giardia (PTGS):

A key step of PTGS is the production of dsRNAs that are homologous with the silenced gene. RT-PCR assays designed to specifically amplify sense or antisense VSP products revealed, after cloning and sequencing these fragments, that RNAs of both strands are present in trophozoites (FIG. 2). To evaluate the possible simultaneous transcription of sense and antisense RNAs for VSP-coding genes, a second nuclear run-on experiment was carried out using specific sense and antisense probes (FIG. 1c). In this assay, it was impossible to detect VSP-antisense RNAs, indicating that those molecules could be generated post-transcriptionally. Products generated by PCR from the WB9B10 clone using vsp9B10 and vsp1267 specific primers were also analyzed (FIG. 1d). The band corresponding to vsp9B10 was present in genomic DNA and sense complementary DNA but poorly in antisense cDNA. In contrast, vsp1267, which is not expressed on the surface of WB9B10 clone, could be amplified from genomic DNA, and equally amplified from both sense and antisense cDNAs. These results demonstrate that VSPs are transcribed simultaneously (further supporting the results of the nuclear run-on experiments), and that there is a low abundance of antisense VSP transcripts that are expressed and a presence of antisense VSPs RNAs that are transcribed but not translated.

Components of the Giardia RNAi Machinery:

RdRP-mediated, unprimed production of dsRNAs from aberrant mRNAs and primed/unprimed production of dsRNA guided by short interfering RNAs (siRNAs) is necessary for triggering RNAi in some organisms. A Giardia homologue of RdRP was identified. This RdRP gene encodes a basic protein of 155,257 Da that shares high homology with other eukaryotic RdRPs and greatly differs from the one encoded by the Giardia virus 16, indicating the protozoan nature of the identified gene.

Giardia RdRP transcription was verified by RT-PCR and northern blotting, and its localization assessed by hemagglutinin-tagged expression (HA). Giardia RdRP is probably associated to ribosomes present on the cytoplasmic side of the endoplasmic reticulum. Moreover, the enzyme is active in trophozoites, because it was capable of forming high-molecular-weight RNAs in vitro in the presence of homologous VSP RNAs (FIG. 3). A characteristic of RNAi is the degradation of dsRNA into 21-25-nucleotide siRNAs by the dsRNA-specific Dicer RNase. Previously, a Giardia Dicer homologue was identified, its structure solved, and the in vitro Dicer activity of the recombinant protein demonstrated (Macrae, I. J. et al. Science 311, 195-198 (2006).

Using the Drosophila Dicer-1 sequence to search for homologous genes in the Giardia genoma database, several clones with high degree of homology with the Dicer domains were identified. By PCR and later comparison with the genomic library, two independent ORF were observed, containing domains present in the known Dicer enzymes: an Argonaute protein with PIWI and PAZ domains (gAgo, GenBank access number AY142142), and bidented RNase III (gDicer, GenBank access number AY142144) containing a PAZ domain and a leucine zipper motif probably implied in the enzyme interaction with other components of RISC and RNA, respectively.

According to what is shown in FIG. 3, the Dicer enzyme expresses constitutively during the complete Giardia life cycle, with cytoplasmic location (FIG. 3). To evaluate the Giardia Dicer activity, in vitro essays were done, wherein radiolabeled dsRNA were exposed to a post-nuclear Giardia extract. The results (FIG. 4a), demonstrated that, regardless of the gene and the strand that is labeled (sense, antisense, or both), dsRNAs are processed into small RNA fragments of 20-30 nucleotides this processing is favored, as in higher eukaryotes, by the presence of ATP (FIG. 4b). small RNAs obtained from those experiments were able to be cloned similar to siRNAs that have 5'-P and 3'-OH ends. Sequencing of those siRNAs indicated that they derived from the input VSP genes and that they are 22-25 nucleotides in length (Table 1).

TABLE 1

| VSP9B10 sense small RNAs | VSP9B10 antisense small RNAs |
|---|---|
| GTTTTGTTCTCGCGGGGGTACTCGT (SEQ ID N° 1) | ACCCCCGCGAGAACAAAACTGCC (SEQ ID N° 57) |
| AGAGCGCGCGGCTCAATGCGCAG (SEQ ID N° 2) | TCCTGCCCATGCAATCTGGACGA (SEQ ID N° 58) |
| GATTGCATGGGCAGGAAAAGCAA (SEQ ID N° 3) | ATTGAGCCGCGCGCTCTGTTGCTTT (SEQ ID N° 59) |
| TCTCGATGTAACACAGGATTTGT (SEQ ID N° 4) | ATGCTTCCTCTGCGCAATTAGTGT (SEQ ID N° 60) |
| GGACAATGTGCAGACNNAGAAGG (SEQ ID N° 5) | CAATACAATTTACCACCGATCAG (SEQ ID N° 61) |
| AAAGATGGCTCCGGAGGCGATACA (SEQ ID N° 6) | TGCACATTGTCCATTGATAGGAA (SEQ ID N° 62) |
| CAGACCTGTGGACAGTGCGCCGAG (SEQ ID N° 7) | CTGATCAGCTGTATCGCCTCCGG (SEQ ID N° 63) |
| CTTTCATGTACAAGGGCGGCTGT (SEQ ID N° 8) | GTAACAGCCGCCCTTGTACATGA (SEQ ID N° 64) |
| CGAAGCANCCCAGCAGCCCGGACAG (SEQ ID N° 9) | CATCTGCCGCCNGACANNTGGTC (SEQ ID N° 65) |
| GCAAGGATACTTCGTGCCGCCGG (SEQ ID N° 10) | CCCGGCGGCACGAAGTATCCTTG (SEQ ID N° 66) |
| ACCAATCGGTCATACCATGCGGAG (SEQ ID N° 11) | ACCGATTGGTGAGAGGCGTCTGC (SEQ ID N° 67) |
| ACGATAAAAAGTACAAGGGCGTGCT (SEQ ID N° 12) | ACTTTTTATCGTTCTTAACTGTTA (SEQ ID N° 68) |
| ACCGGCACCAAGACGTGCAAGAC (SEQ ID N° 13) | TGTGGGAGCGTAACACCGAGTGC (SEQ ID N° 69) |
| TGCGACGTGCGAGAAGGGCGCCGA (SEQ ID N° 14) | CACGCAGTACACGTGGCGGCCTT (SEQ ID N° 70) |
| GCCCGACCCNNAGTGCAACACCCCC (SEQ ID N° 15) | CACGCAGGAGGTGGCTGAGTCCT (SEQ ID N° 71) |
| GCTGCAAGACGTGCAGTGAGCCGA (SEQ ID N° 16) | GTGCCGGTGCACTCTTCTTCTGT (SEQ ID N° 72) |
| AGACAAGCAAGGAGGTGTGCNCA (SEQ ID N° 17) | TTGTTTGGCTGGACCTTCTTATT (SEQ ID N° 73) |
| ACGGTTGTGAGCACCTGGAAGGC (SEQ ID N° 18) | GCACTCACCGTCTCCGGGCACTTT (SEQ ID N° 74) |

TABLE 1-continued

| | |
|---|---|
| CCTGTGCCAAGTGCAATACCTCG (SEQ ID N° 19) | GCTTCTTCGTGCACCCGGTGCCC (SEQ ID N° 75) |
| AGCTACGAAGGAGAGGGCACGGGG (SEQ ID N° 20) | CTGGTGCCCTCGTAGTNNCCTNCC (SEQ ID N° 76) |
| TCGGCCCGCACAGCCTCCTGCCAG (SEQ ID N° 21) | TGAGGACCTGCTTAGGCTCGCAG (SEQ ID N° 77) |
| ACGAAACGACCAANCTCCCTGGAA (SEQ ID N° 22) | CTTCTTGACNCACACGCCGTTCTC (SEQ ID N° 78) |
| TGAATAATGGCGCGCTCATCACTTG (SEQ ID N° 23) | TAGCAGCCCCCGTTCATGCGGAA (SEQ ID N° 79) |
| GATGTAAGACGTGCACCAGCCAG (SEQ ID N° 24) | ACCTCCTCACAGACGCTCTTTCCA (SEQ ID N° 80) |
| TACTACCTGTCCAAAGAAAAGTG (SEQ ID N° 25) | GCTTGTATCCGTCGGCCGGAGTC (SEQ ID N° 81) |
| CCCCCAACCAACAATAAAGGGCC (SEQ ID N° 26) | CACTCGGAGCACCCAGTGGCGCA (SEQ ID N° 82) |
| ACCTCATACAGAACANNAACAGG (SEQ ID N° 27) | CACTTGGTGGCGTCGTCCGCATTG (SEQ ID N° 83) |
| GGGATCTCCGTCGCTGTCATCGC (SEQ ID N° 28) | ACAGCGNCGGAGATCCCCGCTATGG (SEQ ID N° 84) |
| TGCTGGTGGTTCATATGTAGNGG (SEQ ID N° 29) | AGAGGAAGCCCACGAGGCCCCC (SEQ ID N° 85) |
| VSP1267 sense small RNAs | VSP1267 antisense small RNAs |
| GCAAGCACTCTTGCAGGAGCTT (SEQ ID N° 30) | GGCAATTAATTAATAGAAACAT (SEQ ID N° 86) |
| GCTCTACGACTCAGGCTAATTGT (SEQ ID N° 31) | GCTATTAGGCAATTAATTAATAG (SEQ ID N° 87) |
| CAACGGGGTGTGTGAAGCAGCCGC (SEQ ID N° 32) | TTCCGCAACACAATTAGCCTGAG (SEQ ID N° 88) |
| GGCTGCTAATGGTAGTGATAACG (SEQ ID N° 32) | TGCACTTTGTATTACTACTGGCG (SEQ ID N° 89) |
| GTAAGAAGTGCCTTCTGCAAACC (SEQ ID N° 33) | GCACTTCTTACAAGTCTGATCAG (SEQ ID N° 90) |
| CAAACCTTCATGTTCAAGGGCGG (SEQ ID N° 34) | TTAAATTACCAGTNNCTCCCGCT (SEQ ID N° 91) |
| TGATGCTGCCTCTGGTACTACTGG (SEQ ID N° 35) | ATTACTCTCACCAATCGTGACCCC (SEQ ID N° 92) |
| GCGGCTGATACCACGGATTCCTGT (SEQ ID N° 36) | GCGTNATCATTAGGGAAATATCC (SEQ ID N° 93) |
| CAACTGGGGTCACGATTGGTGAG (SEQ ID N° 37) | TTAAGGGNNCTCAGGCTATTCGTG (SEQ ID N° 94) |
| ACTAATTGCGTTNNGTGTACCAAA (SEQ ID N° 38) | TCAGGACAGACCCNGGGTAGCAG (SEQ ID N° 95) |
| GAGTGTGCTTCCAATCTGTATCTG (SEQ ID N° 39) | CGTCGGCGCAGTTTTCCAAATAC (SEQ ID N° 96) |
| GAAACTTGCAAGACAGGATATTTCC (SEQ ID N° 40) | AGTGCAAACTCCGTTGGTTTTATCC (SEQ ID N° 97) |
| TTTCCNTAATGATAACGCTGATA (SEQ ID N° 41) | GCATCGGCTGTCGTGCACAACGT (SEQ ID N° 98) |
| CCGGTGCTATTCTTATCACCTGCA (SEQ ID N° 42) | GCCGCTGGTCTNGACGTAGCAGG (SEQ ID N° 99) |
| GCAAGGACGACAACACTGCGGCC (SEQ ID N° 43) | |
| GTATCGCAGAGTGCACGGGAANG (SEQ ID N° 44) | |
| GGCAGTGCACAGCTAGCATAGCAG (SEQ ID N° 45) | |
| CCTTTGCGTGTCGGCCGAAACAG (SEQ ID N° 46) | |
| TAAAACCAACGGAGTTTGCACTGCC (SEQ ID N° 47) | |
| CTATCAGGCTGAGAAGTTTCCTG (SEQ ID N° 48) | |
| GCAGGAAAGTGCACGACCTGTGCG (SEQ ID N° 49) | |
| VSPH7 sense small RNAs | VSPH7 antisense small RNAs |
| GGAAACCTTGGTAGGATTATTTGC (SEQ ID N° 50) | AGTCGTAGAGCAAGCTCCTGCAAG (SEQ ID N° 100 |
| AATGCTAATCTGTACCTGAAGGCT (SEQ ID N° 51) | ACCCCGTTGATGGGCACATAGTTT (SEQ ID N° 101) |
| GGCATAGATGGGTGCTCTGCATG (SEQ ID N° 52) | CTTCCGTCTTNNAAATAATCCTACC (SEQ ID N° 102) |
| ACAAAGGGAACATGCATTGCAGA (SEQ ID N° 53) | GAATCGTAACCCCGGTTGCGTCG (SEQ ID N° 103) |
| ACGCCGGATAANACCAACGGAGTT (SEQ ID N° 54) | ACTTAGCACAACCGGCCACACCC (SEQ ID N° 104) |
| TGTGCAANNGATAACACTAANA (SEQ ID N° 55) | CTTATCAGCCGTACTACAGGTAAG (SEQ ID N° 105) |
| CTCGTCGGCTTCCTCTGCTGGTG (SEQ ID N° 56) | ACGGTGCTAGCCCTAGTTGTAGA (SEQ ID N° 106) |
| | CGTTCTTCAAGGNNCTCAGATTGTT (SEQ ID N° 107) |
| | CTCTGCAATGCATGTTCCCTTT (SEQ ID N° 108) |
| | CGACCCGGGTGGTGCCGCTCTTGC (SEQ ID N° 109) |
| | CCATTGCTGTCTNTATCTTGCCC (SEQ ID N° 110) |
| | GTGTTATCTTN-GCACACGATGC (SEQ ID N° 111) |
| | GACGGGAGTAGAACTCTGAGGAGA (SEQ ID N° 112) |

The results show that a single *Giardia* Argonaute protein (*Giardia* AGO) could be identified, with PIWI and PAZ domains. Its expression was evaluated by northern blotting and its cellular localization determined by expressing a hemagglutinin tagged version of the protein. *Giardia* AGO localizes to the cytoplasm.

Regulation of VSP Expression:

In the experiments, occurrence of multiple, homologous VSP transcripts could direct the generation of antisense RNAs by *Giardia* RdRP after transcription of several VSP genes took place. Moreover, the presence and activity of Dicer, and probably of AGO, suggests that an RNAi-like mechanism might be involved in regulation of the expression of surface antigenic variants in *Giardia*.

It was analyzed whether the *Giardia* PTGS machinery could discriminate the presence of different VSP mRNAs by mixing *Giardia* cytoplasmic extracts with one, two or three different VSP transcripts generated in vitro. When two or more labeled VSP mRNAs were incubated with trophozoite extracts containing the RNAi machinery, small VSP RNAs were produced, with an identical pattern to the Dicer activity assay products (compare FIG. 4a and FIG. 4c). In contrast, whenever a single transcript was incubated, no mRNA degradation took place. Additionally, if the unrelated genes cwp2 (which encodes the cyst wall protein 2) or gdh (which encodes glutamate dehydrogenase) were added to a single radiolabeled VSP mRNA, no degradation to small RNAs was detected (FIG. 4c), indicating that the silencing machinery specifically processes homologue RNAs. Similar results were obtained when using cell extracts from different *Giardia* clones (for example, WBA6, WB1267 or GSH7): vsp9B10 RNA was processed to small RNAs only when combined with other homologue VSP genes but not when it was the only VSP added to the reaction (FIG. 5). It is evident that the presence in the trophozoite extracts of endogenous siRNAs and various sense and antisense VSP RNAs certainly does not interfere with the silencing process. Because the VSP mRNAs used in these experiments were synthesized in vitro, it is obvious that the silencing mechanism can discriminate among homologous mRNAs in the absence of any possible post-transcriptional RNA modification. Considering that sense and antisense VSP transcripts were found in *Giardia* and that Dicer activity was demonstrated experimentally, small RNAs resulting from VSP dsRNA degradation were searched for.

Using partially a digested vsp9B10 RNA probe for northern blot assays in *Giardia* WB9B10 and WB1267 clones, small RNAs for VSPs that are not expressed (VSP1267 in this case) were detected, but not for the VSP9B10, which is expressed on the surface of the WB9B10 clone (FIG. 4d). These results raise the question of how a single VSP transcript bypasses this silencing process and is translated and expressed at the surface of the parasite.

To prove if the different VSP transcription concentration has a role in the antigenic change, the VSP expression in vivo was unbalanced by the cone expression of both vsp9B10 and vspH7 (GenBank register number, AAA18202), or constructions containing vsp9B10 antisense regions under control of a strong promotor such as de α-tubulin gene (Touz, M. C., Gottig, N., Nash, T. E. & Lujan, H. D. J. Biol. Chem. 277, 50557-50563 (2002) and Elmendorf, H. G. et al. Mol. Biochem. Parasitol. 113, 157-169 (2001)). VSPH7 showed variable expression, even under the pressure of the selection drug, and VSP9B10 also decreased over the time (FIG. 6). Besides, when VSP9B10 was knocked down, its expression on the parasite's surface diminished faster than in the control (FIG. 7). These results suggest that the promoter region of VSPs has little or no influence on VSP expression and, therefore, that a PTGS mechanism must be involved in *Giardia* antigenic variation.

Additional in vitro experiments in which the concentration of different VSP transcripts was unbalanced demonstrated that mRNA concentration may be relevant for a given VSP to circumvent the silencing machinery and be translated (FIG. 8). These results suggest that the *Giardia* extract is programmed to maintain a particular VSP transcript unmodified, but can initiate RNA degradation than when a different VSP is in higher concentration (the processing of a given transcript may depend of the relative cytoplasmic concentration for each VSPs).

Silencing of *Giardia* RdRP, Dicer and AGO:

Since specific gene silencing is not possible in *Giardia* owing to its polyploid and the presence of two nuclei, direct tests to show the involvement of the characterized RNAi components during antigenic variation by knocking down the expression of *Giardia* Dicer, RdRP and AGO by constitutive expression in trophozoites of part of their antisense transcripts were conducted. When a reduction of the expression of RdRP (RdRP-AS) or Dicer (Dicer-AS) took place (FIG. 9), trophozoites that express more than one VSP in their surface were generated, as determined by immunofluorescence assays using specific monoclonal antibodies (FIG. 10a and Table 2), flow cytometry (FIG. 10b) and Western Blot (FIG. 10c). Silencing of *Giardia* AGO did not produce any viable clone, suggesting that this molecule is essential for the parasite. Trophozoites of the invention in which Dicer or RdRP were knocked down proliferate and encyst in culture as normal, and no deleterious effect on VSP regulation when a silencing or knocking procedure was applied (Table 2). From the teachings disclosed here, it is obvious Dicer, RdRP or both can be silenced or knocked out to obtain a modified protozoan, for example a modified *Plasmodium*, *Trypanosoma* protozoan, or any other protozoan showing an antigenic variation mechanism, with all of them within the scope of the present invention.

TABLE 2

Quantitative analysis of vsp expression in *Giardia* with knocked down or silenced RdRP (RdRP-AS) and Dicer (Dicer-AS)

| VSP | None | Mock | *Giardia* RdRP-AS | *Giardia* Dicer-AS |
|---|---|---|---|---|
| VSP9B10 | 99 ± 0.5 | 98 ± 1.2 | 90 ± 0.6 | 18 ± 2.0 |
| VSP1267 | 0 | 0.5 ± 0.1 | 96 ± 0.2 | 22 ± 0.9 |
| VSPA6 | 0 | 0 | 48 ± 2.3 | 17 ± 1.3 |
| VSPS1 | 0 | 0 | 62 ± 4.1 | 36 ± 2.1 |
| VSPS2 | 0 | 0 | 33 ± 1.1 | 28 ± 3.9 |
| VSPS7 | 0 | 0 | 73 ± 0.3 | 65 ± 4.4 |

The table shows percentages of *Giardia* trophozoites expressing a particular VSP as determined by immunofluorescence assays using specific monoclonal antibodies (Mab) (for VSP9B10, Mab 9B10 was used; for VSP1267, 5C1; for VSPA6, 6A7; for VSPS1, 1B2; for VSPS2, 7B8; for VSPS7, 6F8) in WB9B10 trophozoites transfected with antisense constructs of *Giardias* genes codifying for RdRP and Dicer, such as the empty plasmid alone (mock) or not transfected (none) after 5 days culture. Goat anti-mouse immunoglobulins were used as control and showed no reaction. Data are presented as average±SD of 3 independent experiments, each conducted in duplicate. Results indicate, judging from the addition of each percentage, that many different VSP may be expressed by a single trophozoite.

As can be observed in FIG. 10b, the clones showed clear single VSP expression patterns, while RdRP-AS and Dicer-AS trophozoites evidenced the expression of more than one VSP per trophozoite.

As shown in FIG. 10c, specific monoclonal antibody anti-VSP9B10 only recognizes one band in the 9B10 clone and in modified trophozoites, while 12F1 monoclonal antibody of the invention reacts with many protein species in modified trophozoites, indicating that many VSPs may be expressed simultaneously in *Giardia* when the RNAi pathway has been interrupted or silenced.

In summary, a PTGS system (comprising at least RdRP and Dicer) is implicated in the regulation of surface antigen expression in *G. lamblia*. Because a humoral immune response in both experimental and natural *Giardia*-infected hosts coincides with the elimination of the original VSP, a functional role for cells and antibodies in the selection of phenotypic variants and on the course of infection was proposed. Given that parasite protection against specific immune responses relies on switching the expression between immunologically distinct surface proteins, one way in which hosts can prevent infections with a specific immunological response is by producing antibodies against all surface antigenic determinants. These results would demonstrate that the diminished regulation of the RNAi machinery components conducts to expression of more than one surface protein in trophozoites or protozoa, where these modified protozoa constitute a fundamental tool for the generation of a vaccine against important human or animal pathogens, or against any pathogenic microorganism having antigenic variability, for example *Plasmodium* or *Trypanosoma*.

It is evident that independently of the silencing procedure used, any protozoan modified in a way of expressing complete repertoire of surface proteins is enclosed in the scope of the present invention.

Likewise, the present invention encloses in its scope any RdRP and/or Dicer silencing procedure in protozoa.

To determine if modified *Giardia* trophozoites expressing all VSPs repertory could be used as vaccines, studies in an experimental gerbil giardiasis model were conducted. Firstly, trophozoites were generated WB from isolations expressing complete VSP repertoire by knocking down *Giardia* Dicer (DAS) or *Giardia* RdRP (RAS) expression as shown in the examples. Additionally, trophozoite populations expressing only surface VSP were obtained by limiting dilution in WB and GS cell isolations controlled by the use of Mab against given VSPs. FIG. 11 shows that trophozoites where Dicer (FIG. 11a) or RdRP (FIG. 11b) were silenced express many VSPs on their surface, for example as seen in the direct immunofluorescence assays showing co-localization (yellow) of VSP9B10 (green) and VSP1267 (red). As can be seen, most trophozoites express more than one VSP on its surface. Percentage of cells expressing different VSPs on their surface was determined by the use of a panel of monoclonal antibodies directed against different VSP (Table 3)

TABLE 3

| Mab | WB9B10 | DAS | RAS | DAS + RAS |
| --- | --- | --- | --- | --- |
| Control | 0 | 0 | 0 | 0 |
| 9B10 | 99 | 78 | 67 | 75 |
| 5C1 | 0 | 96 | 51 | 93 |
| 6E7 | 0.1 | 89 | 93 | 84 |
| G10/4 | 0 | 0 | 0 | 0 |
| 9C9 | 0 | 0 | 0 | 0 |
| 1B2 | 0 | 66 | 92 | 91 |
| 7B8 | 0 | 89 | 74 | 84 |
| 6F8 | 0 | 87 | 46 | 71 |
| 7G8 | 0 | 90 | 89 | 88 |
| 1B4 | 0 | 77 | 52 | 68 |

These percentages demonstrate that the cells are simultaneously expressed on a great amount of VSPs on their surface (>100%). These modified trophozoites grow and encyst in vitro as wild-type cells, indicating that silencing of these enzymes does not interfere with other cell processes. In culture, trophozoites spontaneously switch from one VSP to another, and therefore, the populations of cells expressing a specific VSP on their surface are maintained exclusively in culture for 24 hs after cloning and selection, in order to insure population homogeneity. FIG. 11c shows that all trophozoites of a non-cloned culture of WB isolates may be labeled (after permeabilization) with the monoclonal antibody of the invention specific for the CRKGA cytoplasmic tail common to all known VSPs. Clonal populations of trophozoites expressing only one VSP (VSP9B10, VSP1267, VSPA6), as determined by indirect immunofluorescence assays contrasted with DAPI, may be observed in FIG. 1d-f (Mab 9B10, Mab 5C1, Mab 6E7, respectively). These *Giardia* populations were initially used to infect SPF gerbils. Infection was initiated orogastric trophozoite inoculation and cyst release, clearly indicating animal infection. *Giardia* cysts were assessed and identified in feces samples by immunofluorescence assays with a specific CWP2 monoclonal antibody (Mab 7D2). In addition, the amount of cysts per gram of feces generated by these animals was counted in order to determine infectivity and virulence of each modified type and wild type cell population. FIG. 12a shows that all populations could establish infection in healthy gerbils. Onset of cyst appearance in feces samples and the amount of cysts varied slightly between different trophozoites used. Some animals were sacrificed and the intestinal content was recovered in order to verify the presence of trophozoites in small intestine. Infected animals showed some diarrhea episodes during the second infection week, and some of them lost weight. In order to prevent the likelihood of some chronically infected animals with small amount of trophozoites, half of the animals were treated with metronidazole to cure any non-detectable infection.

In order to determine if primary infection with trophozoites expressing a particular VSP (VSP9B10 and VSP1267) or with trophozoites expressing complete VSPs repertoire (DAS, RAS, DAS+RAS) protected the animals against later infections, the same animals were inoculated with a clone population of trophozoites expressing a specific VSP (VSP9B10 or VSP1267) 2 months after self-curing the primary infection. FIGS. 12b and 12c show the results of cyst elimination in animals previously infected with WB9B10 or WB1267, respectively. FIGS. 12d and 12e show the results of animals previously infected with DAS or RAS trophozoites, respectively. Results clearly indicate that (a) animals infected with trophozoites expressing one single VSP were refractory to a second infection with cells expressing the same VSP, suggesting the development of a strong immune response during the original infection against a given surface protein (FIGS. 12a and 12b), (b) animals infected with cells expressing a particular VSP were easily re-infected with trophozoites expressing a different VSP, suggesting that, similarly to human infection observations, re-infections are common after cure or medical treatment (FIGS. 12b and 12c). (c) In contrast, animals infected with populations of trophozoites expressing complete VSPs repertoire were protected against later infections with clone populations expressing only one VSP on their surface (FIGS. 12d and 12e). The same experimental challenges were performed 2, 4, 6 and 12 months after the original infection, with identical results (Tables 4 and 5).

TABLE 4

Challenge with WB9B10 clone trophozoites and percentage infected gerbils (between brackets).

| Primary infection with | Number of gerbils | MNZ | Challenge on month 2 (% of infection) | Challenge on month 4 (% of infection) | Challenge on month 12 (% of infection) |
|---|---|---|---|---|---|
| None | 30 | Yes | 30+ (100%) | N/A | N/A |
| None | 30 | No | 30+ (100%) | N/A | N/A |
| WB9B10 | 30 | Yes | 30− (0%) | N/A | N/A |
| WB9B10 | 30 | No | 29− 1+ (3.3%) | N/A | N/A |
| WB1267 | 30 | Yes | 30+ (100%) | N/A | N/A |
| WB1267 | 30 | No | 29+ 1k (100%) | N/A | N/A |
| WBA6 | 30 | Yes | 30+ (100%) | N/A | N/A |
| WBA6 | 30 | No | 30+ (100%) | N/A | N/A |
| Dicer-AS | 90 | Yes | 27− 3+ (10%) | 30− (0%) | 30− (0%) |
| Dicer-AS | 90 | No | 29− 1k (0%) | 28− 2k (0%) | 27− 3k (0%) |
| RdRP-AS | 90 | Yes | 29− 1+ (3.3%) | 29− 1k (0%) | 29− 1k (0%) |
| RdRP-AS | 90 | No | 28− 2+ (6.6%) | 28− 2k (0%) | 29− 1k (0%) |
| Dicer-AS & RdRP-AS | 90 | Yes | 28− 1+ 1k (3.3%) | 30− (0%) | 29− 1+ (3.3%) |
| Dicer-AS & RdRP-AS | 90 | No | 29− 1k (0%) | 29− 1+ (3.3%) | 30− (0%) |

TABLE 5

Challenge with WB1267 clone trophozoites and percentages of infected gerbils (between brackets).

| Primary infection with | Number of gerbils | MNZ | Challenge on month 2 (% of infection) | Challenge on month 4 (% of infection) | Challenge on month 12 (% of infection) |
|---|---|---|---|---|---|
| None | 30 | Yes | 30+ (100%) | N/A | N/A |
| None | 30 | No | 30+ (100%) | N/A | N/A |
| WB9B10 | 30 | Yes | 30+ (100%) | N/A | N/A |
| WB9B10 | 30 | No | 30+ (100%) | N/A | N/A |
| WB1267 | 30 | Yes | 30− (0%) | N/A | N/A |
| WB1267 | 30 | No | 29− 1+ (3.3%) | N/A | N/A |
| WBA6 | 30 | Yes | 30+ (100%) | N/A | N/A |
| WBA6 | 30 | No | 30+ (100%) | N/A | N/A |
| Dicer-AS | 90 | Yes | 28− 2+ (6.6%) | 28− 1+ 1k (3.3%) | 30− (0%) |
| Dicer-AS | 90 | No | 29− 1+ (3.3%) | 29− 1d (0%) | 29− 1k (0%) |
| RdRP-AS | 90 | Yes | 29− 1+ (3.3%) | 29− 1+ (3.3%) | 29− 1+ (3.3%) |
| RdRP-AS | 90 | No | 28− 1+ 1k (3.3%) | 28− 2k (0%) | 30− (0%) |
| Dicer-AS & RdRP-AS | 90 | Yes | 28− 2+ (6.6%) | 29− 1+ (3.3%) | 29− 1k (0%) |
| Dicer-AS & RdRP-AS | 90 | No | 30− (0%) | 30− (0%) | 30− (0%) |

Immunofluorescence assays carried out on feces of selected animals using a monoclonal antibody targeted against *Giardia* CWP2 clearly show cyst release infected animals and absence in those protected (FIG. 13). As can be observed, animals previously infected with WB9B10 clone were refractory to subsequent infection with the same clone (no cysts were found in feces) but they were infected with trophozoites expressing VSP1267 (a high number of cysts was detected). Gerbils previously infected with DAS or RAS trophozoites were protected against subsequent infections with WB9B10 or WB1267 clones (no cysts were found in samples of feces).

To determine if the cysts obtained in original infections (of unknown VSP of released trophozoites) could infect these animals, gerbils previously infected with populations DAS, RAS, and DAS+RAS were inoculated with a great amount of cysts. Table 6 results show that, like animals inoculated with particular trophozoites populations, the animals were refractory to infection, in comparison with control gerbils. Altogether, these results firmly show that an immune response to all VSPs is necessary to prevent generation of new infections.

TABLE 6

Challenge of cyst infection and percentage of infected gerbils (between brackets)

| Primary infection with | Number of gerbils | MNZ | Challenge on month 2 (% of infection) | Challenge on month 4 (% of infection) | Challenge on month 12 (% of infection) |
|---|---|---|---|---|---|
| None | 30 | Yes | 30+ (100%) | N/A | N/A |
| None | 30 | No | 30+ (100%) | N/A | N/A |
| WB9B10 | 30 | Yes | 30+ (100%) | N/A | N/A |
| WB9B10 | 30 | No | 29+ 1k (100%) | N/A | N/A |
| WB1267 | 30 | Yes | 30+ (100%) | N/A | N/A |
| WB1267 | 30 | No | 29+ 1k (96.6%) | N/A | N/A |
| WBA6 | 30 | Yes | 30+ (100%) | N/A | N/A |
| WBA6 | 30 | No | 30+ (100%) | N/A | N/A |
| Dicer-AS | 90 | Yes | 30− (0%) | 30− (0%) | 30− (0%) |
| Dicer-AS | 90 | No | 29− 1k (0%) | 30− (0%) | 29− 1k (0%) |
| RdRP-AS | 90 | Yes | 29− 1+ (3.3%) | 29− 1k (0%) | 29− 1k (0%) |
| RdRP-AS | 90 | No | 29− 1+ (3.3%) | 28− 1+ 1k (3.3%) | 29− 1k (0%) |
| Dicer-AS & RdRP-AS | 90 | Yes | 29− 1+ (3.3%) | 30− (0%) | 30− (0%) |
| Dicer-AS & RdRP-AS | 90 | No | 29− 1+ (3.3%) | 29− 1+ (3.3%) | 29− 1k (0%) |

In addition, symptoms observed during the primary infection disappeared during challenge infection. These results again indicate the need on immune response against all VSPs to prevent new infections.

On the other hand, serum and intestinal content was obtained from infected animals and from control animals, and they were placed in vitro with trophozoites expressing one or several VSPs. Serum or intestinal content of non-infected animals had no effect on parasite morphology, viability, or motility (FIG. 14). In contrast, when a clone population of trophozoites expressing a single VSP was incubated with Mab targeted against said protein or with serum or intestinal content of animals infected with said, disattachment and la agglutination of the whole population occurred, indicating the presence of antibodies against the surface protein. Incubation with serum or intestinal content of gerbils infected with a different clone showed no significant effect (FIG. 14). When a clone population was faced serum or intestinal content from gerbils infected with silenced Dicer or RdRP cells, strong trophozoite agglutination occurred (FIG. 14). These results indicate that infected gerbils were able to develop strong immune response to VSPs present in trophozoites, and other antigens that might be present in the cell surfaces are irrelevant, no only for antibody production but also to confer protection against later infections.

In addition, fluids against trophozoites of isolated GS/M (assembly B). In this case, serum and intestinal content of infected animals with DAS and RAS trophozoites showed partial cell agglutination (between 30 and 40%), indicating that these assemblies may share some common epitopes in their VSPs.

On the other hand, hybridoma lines producing monoclonal antibodies against VSP cytoplasmic tail with the CRKGA amino acid sequence were obtained.

Gerbil Immunization with Purified VSP

The complete VSPs repertoire was purified from modified DAS and RAS trophozoites (see examples) using the monoclonal antibody reacting against the cytoplasmid tail of 5 amino acids present in all VSPs. As control, a Giardia intracellular antigen GRP78/BiP was over-expressed and immunopurified. The animals were then immunized with thises protein preparations, without adjuvant, by in three doses orogastric administration for 3 days. In all cases, vaccination did not cause symptoms of disease, indicating that VSPs alone are not toxic for the animals. After 2 months, the animals were inoculated with parasites expressing particular VSPs. The animal infection was monitored by counting cysts in feces and in some cases sacrificing animals in order to observe the presence of trophozoites in small intestine. Oral immunization with complete VSPs repertoire generates strong immune response, which prevents animal infection; similar results were observed during primary infections. In addition, control animals inoculated with vehicle or GPR78/BiP promptly were infected with clone trophozoite populations (FIG. 15). Individual purified VSPs used as immunogens showed results identical to those observed in infection experiments described above. Protection generated by preparation of complete VSPs repertoire remained for at least a year (Tables 7, 8 and 9).

TABLE 7

Challenge with WB9B10 clone trophozoites and percentage of infected gerbils (between brackets) after immunization with purified VSPs.

| Immunization with VSPs or Bip | Number of gerbils | MNZ | Challenge on month 2 (% of infection) | Challenge on month 4 (% of infection) | Challenge on month 12 (% of infection) |
|---|---|---|---|---|---|
| None | 30 | Yes | 30+ (100%) | N/A | N/A |
| None | 30 | No | 30+ (100%) | N/A | N/A |
| WB9B10 | 30 | Yes | 30− (0%) | N/A | N/A |
| WB9B10 | 30 | No | 28− 2+ (6.6%) | N/A | N/A |
| WB1267 | 30 | Yes | 30+ (100%) | N/A | N/A |
| WB1267 | 30 | No | 30+ (100%) | N/A | N/A |
| WBA6 | 30 | Yes | 30+ (100%) | N/A | N/A |
| WBA6 | 30 | No | 30+ (100%) | N/A | N/A |
| Dicer-AS | 90 | Yes | 25− 5+ (16.6%) | 27− 3+ (10%) | 28− 1+ 1k (3.3%) |
| Dicer-AS | 90 | No | 26− 3+ 1k (10%) | 25− 1+ 4k (3.3%) | 27− 3+ (10%) |
| RdRP-AS | 90 | Yes | 28− 2+ (6.6%) | 28− 1+ 1d (3.4%) | 28− 1+ 1k (3.3%) |
| RdRP-AS | 90 | No | 26− 2+ 2k (6.6%) | 27− 2+ 1k (6.6%) | 30− (0%) |
| Dicer-AS & RdRP-AS | 90 | Yes | 29− 1+ (3.3%) | 29− 1+ (3.3%) | 30− (0%) |
| Dicer-AS & RdRP-AS | 90 | No | 29− 1k (0%) | 29− 1+ (3.3%) | 29− 1k (0%) |
| BiP | 30 | Yes | 30+ (100%) | N/A | N/A |
| BiP | 30 | No | 30+ (100%) | N/A | N/A |

TABLE 8

Challenge with clone WB1267 trophozoites and percentage of infected gerbils (between brackets) after immunization with purified VSPs.

| Immunization with VSPs or Bip | Number of gerbils | MNZ | Challenge on month 2 (% of infection) | Challenge on month 4 (% of infection) | Challenge on month 12 (% of infection) |
|---|---|---|---|---|---|
| None | 30 | Yes | 30+ (100%) | N/A | N/A |
| None | 30 | No | 30+ (100%) | N/A | N/A |
| WB9B10 | 30 | Yes | 30+ (100%) | N/A | N/A |
| WB9B10 | 30 | No | 30+ (100%) | N/A | N/A |
| WB1267 | 30 | Yes | 30− (0%) | N/A | N/A |
| WB1267 | 30 | No | 29− 1+ (3.3%) | N/A | N/A |
| WBA6 | 30 | Yes | 30+ (100%) | N/A | N/A |
| WBA6 | 30 | No | 29+ 1k (100%) | N/A | N/A |
| Dicer-AS | 90 | Yes | 29− 1+ (3.3%) | 27− 2+ 1k (6.6%) | 29− 1+ (3.3%) |
| Dicer-AS | 90 | No | 27− 3+ (10%) | 24− 2+ 4k (10%) | 29− 1+ (3.3%) |
| RdRP-AS | 90 | Yes | 28− 2+ (6.6%) | 29− 1+ (3.3%) | 28− 2k (0%) |
| RdRP-AS | 90 | No | 26− 3+ 1k (10%) | 29− 1+ (3.3%) | 30− (0%) |
| Dicer-AS & RdRP-AS | 90 | Yes | 29− 1+ (3.3%) | 29− 1+ (3.3%) | 29− 1k (3.3%) |
| Dicer-AS & RdRP-AS | 90 | No | 29− 1k (0%) | 29− 1+ (3.3%) | 29− 1+ (3.3%) |
| BiP | 30 | Yes | 30+ (100%) | N/A | N/A |
| BiP | 30 | No | 30+ (100%) | N/A | N/A |

TABLE 9

Challenge of cyst infection and percentage of infected gerbils (between brackets)

| Immunization with VSPs or Bip | Number of gerbils | MNZ | Challenge on month 2 (% of infection) | Challenge on month 4 (% of infection) | Challenge on month 12 (% of infection) |
|---|---|---|---|---|---|
| None | 30 | Yes | 30+ (100%) | N/A | N/A |
| None | 30 | No | 30+ (100%) | N/A | N/A |
| WB9B10 | 30 | Yes | 30+ (100%) | N/A | N/A |
| WB9B10 | 30 | No | 29+ 1k (100%) | N/A | N/A |
| WB1267 | 30 | Yes | 30+ (100%) | N/A | N/A |
| WB1267 | 30 | No | 30+ (100%) | N/A | N/A |
| WBA6 | 30 | Yes | 29+ 1− (96.6%) | N/A | N/A |
| WBA6 | 30 | No | 30+ (100%) | N/A | N/A |
| Dicer-AS | 90 | Yes | 27− 3+ (10%) | 27− 3+ (10%) | 28− 2+ (6.6%) |
| Dicer-AS | 90 | No | 25− 3+2k (10%) | 23− 2+ 5k (10%) | 30− (0%) |
| RdRP-AS | 90 | Yes | 30− (0%) | 28− 1+ 1k (3.3%) | 29− 1+ (3.3%) |
| RdRP-AS | 90 | No | 28− 2+ (6.6%) | 27− 1+ 2k (6.6%) | 29− 1+ (3.3%) |
| Dicer-AS & RdRP-AS | 90 | Yes | 29− 1+ (3.3%) | 29− 1+ (3.3%) | 29− 1k (0%) |
| Dicer-AS & RdRP-AS | 90 | No | 29− 1+ (3.3%) | 29− 1k (0%) | 29− 1k (0%) |
| BiP | 30 | No | 30+ (100%) | N/A | N/A |
| BiP | 30 | No | 30+ (100%) | N/A | N/A |

Interestingly, it must be pointed out that although *Giardia* infection sometimes shows no inflammation, infested gerbil intestines showed increase of size in Peyer patches and in infiltrating neutrophils, mast cells, and lymphocytes in intestinal epithelia (FIG. 16). Gross and microscopic alterations of higher small intestine were not evident in immunized gerbils (FIG. 16).

These results indicate that both initial infection and immunization with VSP preparations can confer immune protection to animals, capable to prevent later infection with *Giardia* cysts or clones obtained from infected person's feces samples.

In all cases, N/A means not applicable, d means sacrificed animals to detect intestinal parasites.

Modified protozoa and the vaccines of the invention increase Ia immunity of any mammal against infections produced by protozoa having antigenic variation mechanisms to overcome host immune response. Evidently, parasites may be any type of protozoa having said mechanism, for example *Plasmodium, Trypanosoma, Babesia*, etc.

Both wild type and modified or silenced protozoa generate an infection with peak cyst excretion on day 15 and self-resolved on day 30.

Animals treated or not with metronidazole showed similar protection pattern to subsequent infections.

Cysts generated by both types of trophozoites, wild and modified (silenced) are infective for native gerbils.

Gerbils infected with live *Giardia* expressing only one VSP on its surface are protected against later infections by the same clone.

Gerbils infected with live *Giardia* expressing only one VSP on its surface are not protected against later infections of different clones.

Gerbils infected with live *Giardia* trophozoites expressing complete VSPs repertoire, for example by silencing Dicer and/or RdRP, are protected against later infection with different clone populations.

Gerbils infected with live *Giardia* trophozoites expressing complete VSPs repertoire, for example by silencing Dicer and/or RdRP, are protected against later infection with cysts obtained from human feces samples.

Gerbils immunized with dead *Giardia* trophozoites expressing complete VSPs repertoire, for example by silencing Dicer and/or RdRP, are protected against later infection with different clone populations.

Gerbils immunized with purified VSPs are protected against later infection with different clone populations.

Gerbils immunized with a purified intracellular antigen are not protected against a later infection.

Primary infection with cells expressing complete VSPs repertoire generates an immunologic response protecting animals against later infections (protection between 87 and 100%).

No vaccine formulation has shown toxic effects on animals.

This invention is better illustrated by the following examples, which must not be construed as a limitation to its scope. On the contrary, it must be clearly understood that other of its embodiments, modifications and equivalents may be referred to, which after reading the present description, may be suggested to those skilled in the art without parting from the spirit of the present invention and/or scope of the enclosed claims.

EXAMPLES

Example 1

Parasite culture and cloning: *Giardia* trophozoites were cultured in TYI-33 medium supplemented with adult bovine serum and bovine bile (Lujan, H. D., Mowatt, M. R., Conrad, J. T., Bowers, B. & Nash, T. E. J. Biol. Chem. 270, 29307-29313 (1995). Continuous cloning of trophozoites was carried out by limiting dilution and selection based on immunofluorescence assays using the corresponding anti-VSP monoclonal antibody. Encystation was carried out as previously reported (Lujan, H. D., Mowatt, M. R., Conrad, J. T., Bowers, B. & Nash, T. E. I, J. Biol. Chem. 270, 29307-29313 (1995). *Giardia lamblia* trophozoites of WB clone strains 9B10, 1267 and A6, and GS clone strain H7 were used.

PCR:

Total *G. lamblia* trophozoite DNA was isolated as described in (Mowatt, M. R. L., H. D.; Cotten, D. B.; Bowers, B.; Yee, J.; Nash, T. E.; Stibbs, H. H. Mol Microbial 15, 955-63 (1995).

a: sense primers S1 (5'-CVT GTG CHR RST GCA A-3') (SEQ ID No 113), S2 (5'-TGC ACS RSC TGC YAB CC-3') (SEQ ID No 114), S3 (5'-TAG TGY DSY VMV TGY AA-3') (SEQ ID No 115) and S4 (5'-CGA TCA TGA CGG GCT TCT-3') (SEQ ID No 116). Antisense primers R1 (5'-CCB ACG AGG CCY CCS ACG AC-3') (SEQ ID No 117) and R2 (5'-CGC CTT CCC KCK RCA KAY GA-3') (SEQ ID No 118). PCR conditions were: denaturalization a t94° C. for 40 s, hybridization at 53° C. for 40 s and elongation at 72° C. for 90 s, using Taq polymerase High Fidelity (Invitrogen) for a total of 35 cycles.

RT-PCR. VSP sense primers (S1-S4) were added to 1 μg of total RNA and heated a t70° C. for 5 min. Reverse transcription reaction samples (2 microliters) were amplified using all possible primer sense/antisense combinations listed above or using specific vsp1267 and vsp9B10 primers (1267_F, 5'-ATG TTG TTG ATA GCC TTC TAT C-3') (SEQ ID No 119); 1267_R, 5'-CTA CGC CTT CCC CCT GCA TAT G-3' (SEQ ID No 120); 9B10_F, 5'-ATG TTT GGC AGT TTT GTT CTC-3' (SEQ ID No 121); 9B10_R, 5'-TCA CGC CTT CCC TCT ACA TAT G-3' (SEQ ID No 122)). RT-PCR products were analyzed by electrophoresis and purified by Qiaex II Gel Extraction Kit (Qiagen). To study expression of different genes during Giardia trophozoite differentiation or in silencing experiments, RT-PCR was used with the following specific pairs of primers: gDicer (645 bp): HL160, 5'-TGG CGG CGT CGT ATC AGT TAT-3' (SEQ ID No 123), HL161, 5'-TCC CCG CAC GCA AGA AGA A-3' (SEQ ID No 124); gAgo (912 bp): HL164, 5'-ATT GCC CCC TAC GGT GTC-3' (SEQ ID No 125), HL165, 5'-CTC TGC CGG CCT TCC TAC-3' (SEQ ID No 126), gRdRP (569 bp): HL187, 5'-CAT GGG TTG CAG TTT CTT GAC GA-3' (SEQ ID No 127), HL188, 5'-AGC CCC TTA TCT GTT GCC TCC TTC-3' (SEQ ID No 128); y CWP1 differential expression control (533 bp): HL183, 5'-TCG CCC TGG ATG TTT CGG ACA T-3' (SEQ ID No 129), HL184, 5'-AGG CGG GTG AGG CAG TA-3' (SEQ ID No 130), and GDH constitutive expression (407 pb): HL185, 5'-AGT GGG GCG GGT CTT TAC TCA-3 (SEQ ID No 131)', HL186, 5'-TGT TCG CGC CCA TCT GGT AGT TCT-3' (SEQ ID No 132). Products of these reactions were also isolated, labeled, and used as probes for Northern blot, as indicated below.

Northern Hybridization:

Total RNA (10-15 µg) was fractionated on a 1.2% agarose-formaldehyde gel, transferred to a Hybond N+ (GE) and fixed with a UV Crosslinker (UVP) by standard procedures. The conserved C-terminal end fragment (anti-sense primer R2) was radioactively labeled with T4 polynucleotide kinase using γ-[32P]-ATP (5'-End Labelling System Promega). grdrp, as well as other DNA fragments, were uniformly labeled by random priming (Prime-A-Gene Labelling System Promega).

Nuclear Run-on Analysis:

cells were resuspended in 1 ml of ice-cold lysis buffer (10 mM Tris-HCl pH 8.4, 1.5 mM MgCl2, 0.14 M NaCl, and Complete™ protease inhibitor cocktail) at 4° C.; 2.25 µl of Nonidet P-40 were added and the suspension was incubated for 15 min on ice. Nuclei were recovered by centrifugation at 2,000 g for 1 min and washed twice in 1 ml of ice-cold nuclei wash buffer (20 mM Tris-HCl pH 8.4, 140 mM KCl, 10 mM MgCl2, 20% (V/V) glycerol and 14 mM (β-mercaptoethanol) at 4° C. Then, nuclei were re-suspended in 50 µl of labeling buffer (20 mM Tris-HCl (pH 8.4 at 4° C.), 140 mM KCl, 10 mM MgCl2, 20% (V/V) glycerol and 14 mM mercaptoethanol, 1 mM each of ATP, GTP, and CTP, 10 mM phosphocreatine, 100 µg/ml phosphocreatine kinase and 0.1 µM [32P]UTP, 5000 µCi/ml) and incubated 2 for 40 min at 37° C. VSP products generated by RT-PCR and 3 µg of vsp9B10, vsp1267, vspH7, and vspaA6 cloned into p-GEM T-easy vector (Promega) were transferred onto Hybond N+ using a slot blot apparatus (BioRad). Additionally, sense and antisense transcripts generated in the in vitro transcription reaction were also blotted under similar conditions.

Detection of Small RNA:

The detection of small RNA was performed as previously reported (35. Hutvagner, G., Mlynarova, L. & Nap, J. P. Detailed, RNA 6, 1445-1454 (2000). Briefly, 15 µg of G. lamblia total RNA was denatured for 10 min at 65° C. in 1× loading buffer, and loaded on a 15% polyacrylamide/7 M urea gel. After electrophoretic separation, RNA was electroblotted in 0.5× Trisborate-EDTA buffer (pH 8) onto a Hybond N+ membrane for 45 min at 100 V in TBE 0.5×, and finally UV fixed. [32P]-labeled riboprobes were transcribed in vitro by T7 or SP6 RNA polymerase using VSPs genes 9B10, 1267 and H7 cloned into p-GEM T-easy vector (Promega). Labeled RNA was partially hydrolyzed during 1 h by incubation at 60° C. in the presence of 80 mM NaHCO3 and 160 mM Na2CO3. Each hydrolyzed VSP transcript was hybridized in 25% formamide, 0.5 NaCl, 25 mM EDTA, 1×Denhardt's solution and 150 µg/ml denatured salmon sperm DNA and incubated at 42° C. overnight. After hybridization the membranes were washed twice in 2×SSC, 0.5% SDS for 30 min and once in 0.5×SSC, 0.5% SDS for 15 min at 45° C. Subsequently, each reverse hydrolyzed vsp transcript was hybridized in the same way and the membranes signals were detected by exposure to Kodak XAR films al—70° C. or a phosphoimager (Amersham). Length standards were from a commercial source (Decade™ RNA markers, Ambion).

Endonuclease Activity:

Dicer activity was analyzed by incubating dsRNA molecules with cytoplasmic extracts of Giardia clone WB9B10, WBA6, or WB1267. vsp9B10, vsp1267, vspH7, cwp2, and gdh genes cloned into p-GEM T-easy vector (Promega) were transcribed in vitro to produce full-length sense [32P]-labeled RNA probes, which were purified and tested for the absence of small RNA contaminants. Pure or mixed vsp transcripts were incubated for 1 h at 37° C. with Giardia extracts. dsRNA was produced by annealing equal amounts in vitro transcribed sense and antisense RNAs (vsp1267, vsp9B10, cwp2 and gdh), labeled or not with [32P] UTP. These dsRNAs were re-suspended in Tris-HCl (pH 7.5)/20 mM NaCl, heated at 95° C. for 1 min and cooled down at room temperature for 12 h. Cell lysates were generated from 1×107-1×108 cells, which were re-suspended in 500 µl of buffer (25 mM Tris-HCl pH 7.5, 250 mM Sucrose, and containing Complete™ protease inhibitor cocktail), sonicated, and centrifuged at 2,000 g for 15 min to separate unbroken cells and nuclei, and then incubated with dsRNA at 37° C. for 1 h. Then, total RNA was extracted, electrophoresed, and transferred as indicated above for small RNA. Selection of low molecular weight RNAs was made by filtration through Microcon-100 filter units. The filtrate, containing small RNAs, was precipitated with 300 mM NaCl/0.6 ml of isopropanol, loaded on a 20% polyacrylamide/7 M urea gel, and electrophoresed. To determine the effects of ATP on the endonuclease activity, ATP was depleted by incubating Giardia cytoplasmic extracts with 2 mM glucose/0.1 U/µl hexokinase (Sigma) for 30 min at ° C. Then, [32P]UTP-labeled vsp1267 dsRNA was added to the lysate in the presence or absence of 10 mM phosphocreatine, 100 µg/ml phosphocreatine kinase, or both, for 1 or 3 h at 37° C. Total RNA was extracted using Trizol and the RNA sample was RNA samples were enriched for low molecular weight RNAs using the Microcon-100 filtration unit as described above. Samples were electrophoresed and products detected as described above. The products of dsRNA processing using Giardia extracts were gel purified, ligated, amplified, cloned, and sequenced (Ngo, H., Tschudi, C., Gull, K. & Ullu, E. Proc. Natl Acad. Sci. USA 95, 14687-14692 (1998).

To determine the nature of the small RNAs, they were treated with alkaline phosphatase (to demonstrate the presence of 5' phosphates) or subjected to periodate oxidation followed by β-elimination (to confirm the presence of 3' hydroxyls), as described (Elbashir, S. M., Lendeckel, W. & Tuschl, T. Genes Dev 15, 188-200 (2001).

RdRP cloning, sequencing, and activity: For RT-PCR, cDNA synthesis was performed using total RNA extracted from trophozoites and oligo(dT)20 as primers. Alignment of the known RdRP from several organisms, in conjunction with codon usage knowledge in Giardia, allowed the design of moderately degenerated primers: RdRP_F: (5'-TA (T/C), GT (T/C) TTT AC (T/C) GAT GGC G (C/G) A GG)-3') SEQ ID No 133 and SEQ ID No 134; and RdRP_R: (5'-TCA CC (A/G) TCC AGG TC (G/A) CTG CC)-3') SEQ ID No 135 and SEQ ID No 136. The PCR product generated using those oligonucleotides was electrophoresed, gel purified, radiolabeled by random priming, and used to screen a G. lamblia cDNA library in λgt22a as reported (Elbashir, S. M., Lendeckel, W. & Tuschl, T. Genes Dev 15, 188-200 (2001). λZAP gDNA library screening was performed as described (Elbashir, S. M., Lendeckel, W. & Tuschl, T. Genes Dev 15, 188-200 (2001). DNA fragments were cloned into pBlueScript SKII+ and submitted for automatic sequencing. 3 5'-RACE was performed using a commercial kit from Invitrogen and primers 5'-CTT GTG CAT AGT AAA CAA AG-3' SEQ ID No 137 and 5'-CAA ATG GTC GAT GCT GGG-3' SEQ ID No 138. For gRdRP activity in vitro, HA-tagged RdRP was purified from transfected trophozoites by affinity using antiHA-sepharose (Sigma). Enzyme activity was assayed at 35° C. for 60 min in 20 μl reaction mixture containing 50 mM Hepes pH 7.6, 20 mM ammonium acetate, 5 mM MgCl2, 0.1% Triton X-100, 1 mM each of four ribonucleoside triphosphate (including [α-32P] UTP), and 1 u/μl RNasin, plus the addition of ssRNA substrates (250 μg/ml) prepared by in vitro transcription as described, with or without the presence of VSP specific primers. Reaction products were analyzed by agarose gel electrophoresis followed by transfer and autoradiography.

Transfection and Immunofluorescence Assays:

Plasmid PTubPac37 was modified to introduce the entire gRdRP, gDicer, gAgo, and VSPH7 coding regions and, when corresponding, the Influenza Haemaglutinin epitope (HA) before the TAA stop codon (Touz, M. C., Gottig, N., Nash, T. E. & Lujan, H. D. J. Biol. Chem. 277, 50557-50563 (2002). gAgo coding region was introduced into the plasmid pTubNterPac in which the gene is introduced after the Haemaglutinin coding region to avoid possible interference of the HA tag with the PIWI domain. This plasmid is a modification of the pTubHAPac with the substitution of the original multiple cloning site by a new one (MCSnewSense: 5'GAT TCC GGG CCC AGATCT ATC GAT ACG CGT ATG CAT TCG CGA GAT ATC TGC 3' SEQ ID No 139; MCSnewAntisense: 5'GCG GCC GCA GAT ATC TCG CGA ATG CAT ACG CGTATC GAT AGA TCT GGG CCC G 3' SEQ ID No 140). La transfection of trophozoites of G. lamblia was done by electroporation as already described (Yee, J. & Nash, T. E. Proc. Natl Acad. Sci. USA 92, 5615-5619 (1995). Transfection of G. lamblia trophozoites was done by electroporation as previously described38. Cells were incubated on ice for 10 min, cultured in growth medium overnight at 37° C. and selected as puromycin-resistant cells. Indirect immunofluorescence assays using an anti-HA monoclonal antibody (Sigma) was performed on non-encysting trophozoites fifteen days after transfection as described (Touz, M. C., Gottig, N., Nash, T. E. & Lujan, H. D. J. Biol. Chem. 277, 50557-50563 (2002). Previously reported anti-VSP monoclonal antibodies were used to test the expression on different VSP on fixed trophozoites as described elsewhere (Touz, M. C., Gottig, N., Nash, T. E. & Lujan, H. D. J. Biol. Chem. 277, 50557-50563 (2002). Novel monoclonal antibodies generated in this study were used similarly. Confocal images were collected using a Zeiss LSM5 Pascal laserscanning confocal microscope equipped with an argon/helium/neon laser and a ×100 (numerical aperture=1.4) oil immersion objective (Zeiss Plan-Apochromat). Single confocal sections of 0.3 μm were taken parallel to the coverslip (z sections). Images were acquired using a Zeiss charge-coupled device camera and processed with LSM and Adobe Photoshop software. For functional analysis of gRdRP, gDicer, and gAgo, and VSP9B10 specific sense primers containing an Eco RV site and antisense primers with an Nco I site were used to amplify by PCR the a portion of the ORF of each gene. PCR products were purified, restricted, and cloned into the vector pTubHAPac. In this manner, genes were inversely inserted inside pTubHAPac, giving the antisense construct that was then used for inhibition of expression (Touz, M. C., Gottig, N., Nash, T. E. & Lujan, H. D. J. Biol. Chem. 277, 50557-50563 (2002). Sequences were always confirmed by dye terminator cycle sequencing. Gene knock-downs were confirmed by RT-PCR and qRT-PCR using the gene specific primers indicated above on total RNA extracted from transfected trophozoites and compared to control of cells transfected with vector only or with the same vector expressing an HA-tagged version of each molecule.

Example 2

Production of Monoclonal Antibodies to the VSPs 5 Amino Acid of and to Individual VSPs Six week-old female BALB/c mice were immunized subcutaneously with either 200 mg of (a) an HPLC purified preparation of NH2-CRGKA-COOH peptide conjugated to KLH using the sMBS cross-linker, or (b) the synthetic multiple antigen peptide [NH2-CRGKA]8-[K]7-bAla-OH (both from Biosynthesis, Inc.), or protein extract of cultured trophozoites derived from the WB isolate, emulsified in Sigma adjuvant system (Sigma). Mice were boosted subcutaneously after 21 days with 200 mg of the same preparation, and 20 days later boosted intravenously with 100 mg of the antigen preparation. Three days later, the mice were euthanized and the spleen cells used for fusion to NSO myeloma cells. Hybridomas secreting antibodies were screened by ELISA using the original peptides and by indirect immunofluorescence using nonencysting and encysting trophozoites (Jambhekar, A. D. et al. RNA 13, 625-642 (2007) and Aggarwal, A., Merritt, J. W., Jr. & Nash, T. E. Cysteinerich; Mol Biochem Parasitol 32, 39-47 (1989)). Monoclonal antibodies against VSP were generated using entire trophozoites as previously reported (Mowatt, M. R. L., H. D.; Cotten, D. B.; Bowers, B.; Yee, J.; Nash, T. E.; Stibbs, H. H. Mol Microbiol 15, 955-63 (1995).

DNA Methylation:

from G. lamblia clone 1267 was purified by extraction with phenol and chloroform/isoamyl alcohol (24/1% v/v), incubated with ARNase (Roche) to eliminated ARN contamination, and precipitated with ethanol. The presence of methyl deoxyribonucleosides was determined by high-performance liquid chromatography HPLC (45, 46). The separation of deoxyribonucleosides was performed on a Phenomenex Luna 5 μm C18, 4.6×150 mm. The method was calibrated based on the absorption of standard deoxyribonucleosides of known concentration.

Example 3

Preparation of the Different Vaccines and Protection Assays

1. Parasites:

*Giardia lamblia* WC strain (ATCC 30957) was isolated from a symptomatic patient believed to have acquired giardiasis in Afghanistan (Antigenic analysis of *Giardia lamblia* from Afghanistan, Puerto Rico, Ecuador, and Oregon. Smith P D, Gillin F D Kaushal N A and Nash T E. Infect. Immun. 1982 May; 36(2): 714-9), and the GS/M strain was isolated from a symptomatic patient from USA (Antigenic analysis of *Giardia lamblia* from Afghanistan, Puerto Rico, Ecuador, and Oregon. Smith P D, Gillin F D Kaushal N A and Nash T E. Infect. Immun. 1982 May; 36(2): 714-9), clones derived from WB strain, and the transgenic trophozoites were cultured at 37° C. in TYI-S-33 medium supplemented with 20% adult serum (Invitrogen), bovine bile (Sigma), and a antibiotic/antimycotic solution (Invitrogen) in 12 ml borosilicate glass tuber with threaded cap (Methods for cultivation of luminal parasitic protists of clinical importance. Clark C G, Diamond L S. Clin Microbiol Rev. 2002 July; 15(3):329-41). *Giardia* clones expressing different surface proteins were obtained by limiting dilution in 96-well culture plates (DeltaLabs) in an anaerobic chamber (BD) and selected by immunofluorescence assays using specific monoclonal antibodies (A new method for cloning *Giardia lamblia*, with a discussion of the statistical considerations of limiting dilution. Baum K F, Berens R L, Jones R H, Marr J J. J Parasitol. 1988 April; 74(2): 267-9). Reactive clones were amplified overnight in culture medium and homogeneity was verified before use. WB 1267 (Mab 5C1), 9B10 (Mab 9B10), A6 (Mab 6E7) and GS/M/H7 (Mab G10/4) clones were used in control experiments and in infections (Nash, T. Surface antigen variability and variation in *Giardia lamblia*. Parasitol Today 8, 229-234 (1992).

Generation of Transgenic Trophozoites Expressing Complete VSPs Repertoire:

Complementary sequences to the genes codifying for *Giardia* RdRP and Dicer enzymes were cloned in pTub-HA.pac plasmid (Sorting of encystation-specific cysteine protease to lysosome-like peripheral vacuoles in *Giardia lamblia* requires a conserved tyrosine-based motif. Touz M C, Lujan H D, Hayes S F, Nash T E. J Biol Chem. 2003 Feb. 21; 278(8):6420-6. Epub 2002 Dec. 3. This allowed for constitutive and stable gene expression in *G. lamblia* trophozoites due to the presence of α-tubulin promotor and selection with the antibiotic puromycin. Genes codifying Dicer and RdRP enzymes were amplified by PCR from WB/9B10 clone cDNA using Platinum HiFi Taq DNA polymerase (Invitrogen), using oligonucleotide probes containing NcoI and EcoRV restriction sites and then cloning the vector. Primers were DAF: 5'-AGT TGA AAC TAT CAT GGT TGC TCC CGA A-3' SEQ ID No 141, DAR: 5'-CCA CCA TGG TTG AAC GCC GAA TCC AAC-3' SEQ ID No 142, RAF: 5'-GCG ATA GGT TGC AGT TCC ATG ACG TTC TTG A-3' SEQ ID No 143, and RAR: 5'-CCA CCA TGG TCG CTA CCT TAG CAT CAT CC-3' SEQ ID No 144. Constructions were verified by digestion with restriction enzymes and later sequencing. Enzyme silencing verification was carried out by qRT-PCR as described above.

*Giardia lamblia* Transfection:

*Giardia* transfection was performed by electroporation, essentially as reported (Transient transfection and expression of firefly luciferase in *Giardia lamblia*. Yee J, Nash T E. Proc Natl Acad Sci USA. 1995 Jun. 6; 92(12):5615-9).

Briefly, WB/9B10 clone trophozoite cultures growing until confluence in 12-ml tubes (about $10^7$ cells) were re-suspended in 0.3 ml complete TYI-S-33 medium, in 0.4 cm plates. Then, 10-15 μg plasmid were added to a final volume of 100 μl. The mixture was incubated for 10 minutes on ice. Cells were electroporated at 350V, 1000 μF and 700Ω in a BTX electroporator. After incubation on ice for 10 minutes, the cells were transferred to a tube containing a 12 ml complete medium and incubated overnight at 37° C. in anaerobiosis. Next day, the medium was complemented with puromycin and trophozoites were incubated for 7-10 days at 37° C. To obtain clone cell lines, limiting dilution was performed in 96 well plates.

Confocal Immunofluorescence and Microscopy:

Trophozoites were detached from the tubes by cooling down for 20 minutes in ice. The cells were recovered and re-suspended in growth medium, applied on glass slide p se incubated at 37° C. in humid camera for 1 hour to allow for trophozoites re-adhering. Preparations were washed with warm medium three times, plus two washings in warm PBS. Then, cells were turned permeable by fixation with 1:1 acetone/methanol for 30 minutes at −20° C. and blocked in 1× PBS/0.05% Tween 20, BSA 2.5% for 30 min. Cells were firstly incubated with Mab against different VSPs diluted in 1× PBS/0.05 Tween 20, BAS 2.5% for 1 hour at room temperature. Monoclonal antibodies targeted against different VSPs were: mAb 9B10 (anti VSP-9B10B), mAb 5C1 (anti-VSP 1267), mAb 6E7 (anti-VSP A6), mAb 1B2 (anti-VSP S1), mAb 2D5 (anti-VSP S2), mAb 2E1 (anti-VSP S3), mAb 2G10 (anti-VSP S4), MAb 6F8 (anti-VSP S5), mAb 7A9 (anti-VSP S6), mAb 7B8 (anti-VSP S7), mAb 7C2 (anti-VSP S8), mAb 7C9 (anti-VSP S9), mAb 7C10 (anti-VSP S10), mAb 7D4 (anti-VSP S11), mAb 2D4 (anti-VSP S12), mAb 3B8 (anti-VSP S13), mAb 4A2 (anti-VSP S14), mAb 7F4 (anti-VSP S15), Mab 7H2 (anti-VSP S16). After incubation with the appropriate monoclonal antibody, the slides were washed twice with 1×PBS/0.05 Tween 20, and then incubated with a second goat anti-mouse immunoglobulin antibody labeled with FITC or TRITC in a 1/200 dilution for 1 hour in blocking solution. Nuclei were contrasted with DAPI. Confocal images were obtained by a laser confocal microscope LSM5 Zeiss Pascal equipped with a argon/helium/neon laser, and an oil immersion objective× 100 (numerical aperture=1.4) (Zeiss Plan Apochromat). 0.3 micron confocal sections were taken parallel to the cover slide (sections z). Images were obtained using a Zeiss camera by the device and processed with LSM and Adobe Photoshop software. The percentage of cells expressing a particular VSPs was computed by counting 500 cells in triplicate experiments or by flow cytometry.

Production of Monoclonal Antibodies Against 5 Amino Acid VSPs Tail:

Production of monoclonal antibodies to the 5-amino acid VSPs tail was carried out as described above in example 2.

2. Polyacrylamide Gel Electrophoresis and Western Blotting:

Protein trophozoite extract were subjected to polyacrylamide gel electrophoresis (SDS-PAGE) and Western Blot as reported (Lujan, H. D., Mowatt, M. R., Conrad, J. T., Bowers, B. & Nash, T. E. Identification of a novel *Giardia lamblia* cyst wall protein with leucine-rich repeats. Implications for secretory granule formation and protein assembly into the cyst wall. *J Biol Chem* 270, 29307-29313 (1995).

Animals:

All procedures carried out in animals were performed in accordance with protocols approved by the Institution Commission of Care and Use of Animals of Universidad Católica de Córdoba and the immunization guideline was well tolerated by all animals. Male endogenously breed gerbils, 6-weeks old pathogen free specimens (SPF) (*Meriones unguiculatus*) were obtained from Bioterio de animales de investigación of Universidad Católica de Córdoba and individually housed in an air-conditioned (18-22° C., 40-50% humidity) biohazard rack (Techniplast) with a 12-hour-light, 12-hour-dark cycle. They were given autoclaved food and sterile water supplemented with a mixture of filter-sterilized vitamin solution ad libitum. In this study, only animals born in our premises were used, in order to assure that they were never infected with the *Giardia* parasite or any other related. All animals were kept under SPF laboratory conditions according to the rules and rulings of the Argentine Council of Animal Care and international animal attention rules. Before infection, gerbils were tested for negativity of serum antibodies against *Giardia lamblia* or proteins of *Giardia* by ELISA using a preparation of total proteins extracted from trophozoites and cysts. After infections, some control groups of gerbils were orally treated with 20 mg Metronidazole for 3 days, 10 days antes before challenges to rule out any possible presence of low level of intestinal *Giardia*

Elimination of Protozoa Parasites by Treatment with Metronidazole:

To initiate treatment, the animals were placed in sterile cages with filtered air; water and food were sterilized in autoclave. A 100 mg/ml Metronidazole working solution was prepared. 500 µl of this solution was given orally to the animals in one daily dose for three consecutive days. The animals did not receive antibiotics the following four days. Treatment continued for dos days with 500 µl of metronidazole working solution. Treatment was complemented by the addition of 2 ml metronidazole in 400 ml of autoclaved drinking water, which was the only water the animals could drink during the whole treatment (animals ingest this diluted metronidazole solution for nine days). Feces were collected daily during the whole treatment and microscopic control by immunofluorescence assays were done with monoclonal antibody 7D2 (cyst wall anti-protein 2? (Identification of a novel *Giardia lamblia* cyst wall protein with leucin-rich repeats. Implications for secretory granule formation and protein assembly into the cyst wall. Lujan H D, Mowatt M R, Conrad J T, Bowers B, Nash T E. J Biol Chem. 1995 Dec. 8; 270(49):29307-13) every day in order to determine the presence of cysts. During the treatment, the normal animal flora suffered increase of yeasts, and recovered its normal status few days after finishing treatment.

3. Infections:

Infections were induced in gerbils by orogastric inoculation of $2 \times 10^5$ trophozoites or cysts resuspended in 0.5 ml of phosphate-buffered saline (PBS). Some control animals received 0.5 ml of PBS by the same route. Fresh cysts collected from infected gerbils were used in order to prevent rapid loss of viability and infectivity produced in samples obtained from infected patients. Fecal collection from infected gerbils was performed daily from day 0 to day 30. Cysts or trophozoites were identified visually by light microscopy or by immunofluorescence assays using cyst (mAb 7D2) or trophozoite-specific antigens (BIP; Mab 9C9).

4. Periodically, randomly selected gerbils were sacrificed, the small intestines were isolated, slit opened longitudinally and suspended in culture medium at 4° C. for 30 min. The supernatants were collected and examined for *Giardia* trophozoites by light and fluorescence microscopy or placed in culture medium up to six days as reported (Gottstein, B., Deplazes, P. & Tanner, I. In vitro synthesized immunoglobulin A from nu/+ and reconstituted nu/nu mice against a dominant surface antigen of *Giardia lamblia*. Parasitol Res 79, 644-648 (1993)).

*Giardia* cysts excreted by gerbils were quantified by collecting stool pellets from individually housed animals over a 24-hour period. The stool samples were weighted, resuspended in 2 ml of PBS, and filtered through 3 layers of cheesecloth. Filtrate was centrifuged at 250 g during 10 min in a refrigerated centrifuge (Beckman). The filtrate was centrifuged at 250 g for 10 min in a refrigerated centrifuge (Beckman) at 4° C. After 3 washes, the pellet was suspended in 2 ml of PBS; cysts stained with FITC-labeled 7D2 mAb, and counted in a hemacytometer. Gerbils were deemed not infected if no cyst was found in feces or if no trophozoite was detected after 6 days culture.

Purification of VSPs from Dicer-AS and RdRP-AS Transgenic Trophozoites:

Complete repertoire of VSPs expressed in these transgenic trophozoites generates as described were purified by immunoaffinity using Mab 12F1 of the invention generates against the 5 amino acids of the conserved VSP tail. Protein A-Sepharose (Amersham) was used to isolate the mouse immunoglobulins from ascites fluid produced by IP injection of a culture of hybridoma cells. Purified mAb was linked to magnetic beads (Dynal) and utilized to purify VSPs from plasma membrane-containing microsomal fractions of trophozoites. Purified VSPs were re-suspended in PBS containing 0.01% Tween 20, quantified, and used to immunize gerbils orally. Individual VSPs were purified by the same methodology using specific mAbs.

Purification of *Giardia* GRP78/BiP:

*G. lamblia* trophozoites isolated from 9B10 WB clone were transfected with plasmid pTubHA.pac containing the complete length of *Giardia* endoplasmic reticulum chaperone BiP/GRP78 (Increased expression of the molecular chaperone BiP/GRP78 during differentiation of a primitive eukaryote. Lujan H D, Mowatt M R, Conrad J T, Nash T E. Biol Cell. 1996; 86(1):11-8) and three copies of this epitope was labeled with Haemagglutinin (HA-BIP). Transgenic trophozoites were lysated with buffer RIPA and the isolated BIP protein using anti-HA immunopurification kit (Sigma).

Oral Immunization:

The animals were immunized with three successive oral administrations of 200 µg parasite proteins suspended in sterile PBS/0.01% Tween 20, with three days difference between each administration. The same amount of proteins was administered to the gerbils when BIP, membrane preparations, or purified VSPs were used as immunogens.

Blood Samples:

Blood samples were collected after the first day of infection or immunization to detect the presence of circulating antibodies as described below. Gerbils were anesthetized with ether and blood was taken from the orbital plexus or by intracardial puncture. Serum was collected by blood sample centrifugation at 800×g for 15 min and stored at −70° C. until use. Gerbils were sacrificed with gaseous carbon dioxide.

5. Intestinal Contents:

Small intestine secretions of infected, not infected and immunized gerbils were collected as in mice (Heyworth, M. F. Relative susceptibility of *Giardia muris* trophozoites to killing by mouse antibodies of different isotypes. *J Parasitol* 78, 73-76 (1992)).

In summary, gerbils fasted during a day with access to water and then sacrificed. The small intestine was excised from duodenum to cecum and its content was aspirated with a syringe and separated. En some cases, the intestinal content was centrifuged at 5,000×g at 4° C. to separate cells, rests, and bacteria. En some experiments, the small intestine lumen was washed five times with 3 ml of cold PBS and centrifuged as described above. Supernatants were sterilized by filtration and stored at −70° C. until use.

Agglutination Assays:

Assays were performed in 96-well plain bottom plates. About 5×10⁵ trophozoites were incubated at 4° C. for 1 h with several dilutions of animal intestinal secretions, serum, or ascetic fluid containing specific antibodies against VSPs (all heat-inactivated) in TYI-S-33 medium without adult bovine serum. They were mixed and trophozoite agglutination was assayed by microscopy. Linking of antibodies to the parasite surface was demonstrated with goat anti=mice immunoglobulins labeled TRITC.

The invention claimed is:

1. A vaccine against infections produced by *Giardia* protozoan parasite, characterized by comprising at least modified *Giardia* protozoan parasite having antigenic variation modified only by having the gene RNA-dependent RNA polymerase (RdRP), or the Dicer gene, or both silenced, expressing on its surface more than one variable surface protein, and excipients and/or adjuvants.

2. The vaccine of claim 1, characterized by the modified *Giardia* protozoan parasite expressing on its surface the complete repertoire of variable surface proteins.

3. A vaccine, against infections produced by *Giardia* protozoan parasite, characterized by comprising more than one variable surface protein of modified *Giardia* protozoan parasite having antigenic variation modified only by having the gene RNA-dependent RNA polymerase (RdRP), or the Dicer gene, or both silenced, wherein each of said proteins is different; excipients and/or adjuvants.

4. The vaccine of claim 3, characterized by comprising the complete repertoire of variable surface proteins, wherein each of said proteins is different.

5. An immunization method for immunizing a mammal against infections produced by *Giardia* protozoan parasite, comprising administering to the mammal an amount of a vaccine in accordance with claim 1.

6. The method of claim 5, wherein the vaccine is administered in a form selected from the group consisting of oral, subcutaneous, intravenous and intramuscular.

7. An immunization method for immunizing a mammal against infections produced by *Giardia* protozoan parasite, comprising administering to the mammal an amount of a vaccine in accordance with claim 3.

8. The method of claim 7, wherein the vaccine is administered in a form selected from the group consisting of oral, subcutaneous, intravenous and intramuscular.

* * * * *